US009708265B2

(12) United States Patent
Tovbin et al.

(10) Patent No.: US 9,708,265 B2
(45) Date of Patent: Jul. 18, 2017

(54) URETHANES, UREAS, AMIDINES AND RELATED INHIBITORS OF FACTOR XA

(76) Inventors: Dmitry Gennadievich Tovbin, Moskovskaya obl. (RU); Dmitry Nikolaevich Tarasov, Moskovskaya obl. (RU); Dimitry Viktorovich Malakhov, Moscow (RU)

( * ) Notice: Subject to any disclaimer, the term of this patent is extended or adjusted under 35 U.S.C. 154(b) by 0 days.

(21) Appl. No.: 13/599,038

(22) Filed: Aug. 30, 2012

(65) Prior Publication Data
US 2013/0005778 A1    Jan. 3, 2013

Related U.S. Application Data

(63) Continuation of application No. PCT/RU2011/000129, filed on Mar. 2, 2011.

(30) Foreign Application Priority Data

Mar. 3, 2010  (EA) .................................. 201000506

(51) Int. Cl.
| | | |
|---|---|---|
| A61K 31/44 | (2006.01) |
| A61K 31/415 | (2006.01) |
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |
| C07D 403/02 | (2006.01) |
| C07D 233/00 | (2006.01) |
| C07D 213/75 | (2006.01) |
| A61K 31/16 | (2006.01) |
| A61K 31/17 | (2006.01) |

(52) U.S. Cl.
CPC ............ C07D 213/75 (2013.01); A61K 31/16 (2013.01); A61K 31/17 (2013.01)

(58) Field of Classification Search
CPC .............................. C07D 213/00; A61K 31/44
See application file for complete search history.

(56) References Cited

U.S. PATENT DOCUMENTS

| 4,588,587 A | 5/1986 | Gasic |
| 6,967,208 B2 | 11/2005 | Pinto et al. |
| 7,727,982 B2 | 6/2010 | Zhu et al. |
| 2002/0002183 A1 | 1/2002 | Zhu et al. |
| 2003/0153610 A1 | 8/2003 | Straub et al. |

FOREIGN PATENT DOCUMENTS

| EP | 0798295 | 10/1997 |
| RU | 2003121018 A | 12/2004 |
| WO | WO 98/28269 | 7/1998 |
| WO | WO 99/10316 | 3/1999 |
| WO | WO 0119788 | 3/2001 |
| WO | WO 0144172 | 6/2001 |
| WO | WO 03/048158 | 6/2003 |
| WO | WO 03/048158 A1 * | 6/2003 |
| WO | WO 2006070878 | 7/2006 |
| WO | WO 2008073670 | 6/2008 |

OTHER PUBLICATIONS

Rameshwar, N. et al. QSAR studies of N1-(5-chloro-2-pyridyl)-2{[4-(alkyl methyl)benzoyl]amino}-5-chlorobenzamide analogs. Bioorganic & Medicinal Chemistry. 2006, vol. 14, pp. 320-321, table 1, compounds 32 and 36.*
Rameshwar, N. et al. QSAR studies of N1-(5-chloro-2-pyridyl)-2-{[4-(alkyl methyl)benzoyl]amino}-5-chlorobenzamide analogs. Bioorganic & Medicinal Chemistry. 2006, vol. 14, pp. 320-321.*
Zhang, P. et al. Design, synthesis, and SAR of anthranilamide-based factor Xa inhibitors incorporating substituted biphenyl P4 motifs. Bioorganic & Medicinal Chemistry Letters. 2004, vol. 14, pp. 986.*
Claeson, G.,"Synthetic Peptides and Peptidomimetics as Substrates and Inhibitors of Thrombin and Other Proteases in the Blood Coagulation System", Blood Coag. Fibrinol. 5, 411-436 (1994),abstract.
Turner, A. D. et al.,"p-Amidino Esters as Irreversible Inhibitors of Factor IXa and Xa and Thrombin", Biochemistry, 25, 4929-4935 (1986), abstract.
Hitomi, Y. et al.,"Inhibitory Effect of New Synthetic Protease Inhibitor (FUT-175) on the Coagulation System", Haemostasis, 15, 164-168 (1985), abstract.
Hauptmann, J. et al.,"Comparison of the Anticoagulant and Antithrombotic Effects of Synthetic Thrombin and Factor Xa Inhibitors", Thromb. Haemost., 63, 220-223 (1990), abstract.
Tidwell, R. R. et al.,"Strategies for Anticoagulation With Synthetic Protease Inhibitors. Xa Inhibitors Versus Thrombin Inhibitors", Thromb. Res., 19, 339-349 (1980).
Sturzebecher, J. et al.,"Synthetic Inhibitors of Bovine Factor Xa and Thrombin. Comparison of Their Anticoagulant Efficiency", Thromb. Res., 54, 245-252.
Kam, C. M. et al.,"Mechanism Based Isocoumarin Inhibitors for Trypsin and Blood Coagulation Serine Proteases : New Anticoagulants", Biochemistry, 27, 2547-2557 (1988).

(Continued)

*Primary Examiner* — Rita Desai
*Assistant Examiner* — Ben S Michelson
(74) *Attorney, Agent, or Firm* — SciTech Legal, P.C.; Yakov M. Korkhin, Esq.

(57) ABSTRACT

The invention relates to a new class of compounds, their pharmaceutically acceptable salts and pharmaceutically acceptable compositions that are effective as selective inhibitors of factor Xa, both in the isolated state and in a complex with other proteins. The compounds of the invention can be used for treating and preventing diseases, such as acute coronary syndrome, myocardial infarction, unstable angina, refractory angina, thromboses caused by post-thrombolytic therapy or coronary angioplasty, acute ischemia mediated cerebrovascular syndrome, embolic stroke, thrombotic stroke, and other diseases in humans and other mammals associated with blood coagulation problems.

25 Claims, No Drawings

(56) References Cited

OTHER PUBLICATIONS

8. Jordan, S. P.; Waxman, L.; Smith, D. E.; Vlasuk, G. P. Biochemistry 1990, 29, 11095.
9. Morrison, J. F. Biochim. Biophys. Acta 1969, 185, 269.
David B. Troy, Joseph Price Remington. Remington's <<The Science and Practice of Pharmacy>>. 21st edition, Baltimore, MD: Lippincott Williams & Wilkins, 2006, pp. 745-766.
Kirk Othmer's <<Encyclopedia of Chemical Technology>>, John Wiley and Sons, 2007.
Brunton Laurence L., <<Goodman and Gilman's. The Pharmacological Basis of Therapeutics>>, The McGraw-Hill Companies, 2010.
PCT/RU 2011/000129 International Search Report and Written Opinion of Jun. 30, 2011.

\* cited by examiner

URETHANES, UREAS, AMIDINES AND RELATED INHIBITORS OF FACTOR XA

RELATED APPLICATIONS

This application is a continuation of International Patent Application No. PCT/RU2011/000129, filed Mar. 2, 2011, which claims priority to Eurasian Patent Application No. 201000506, filed Mar. 3, 2010, both of which are incorporated herein by reference in their entirety.

FIELD OF THE INVENTION

This invention relates to a new class of compounds, which are potent and highly selective inhibitors of factor Xa, both isolated and when assembled in a complex with other proteins. In another aspect the invention relates to a new class of compounds, their pharmaceutically acceptable salts, and pharmaceutically acceptable compositions thereof, which are useful as potent and selective inhibitors of blood coagulation in humans and other mammals. In yet another aspect, the invention relates to new methods for using new classes of agents for treating diseases associated with coagulation disorders in humans and other mammals.

BACKGROUND OF THE INVENTION

Hemostasis, the control of bleeding, is effectuated either by surgical means or by affecting the physiological state of blood vessels or the coagulation. This invention particularly concerns blood coagulation and its role in maintaining the functioning of the human organism after injury, inflammation, disease, congenital defect, dysfunction, or other disruption.

Thrombin is a key protein responsible for the coagulation.

Thrombin plays the main role in thrombosis due to its ability to catalyze the conversion of fibrinogen into fibrin.

Direct and indirect inhibitors of thrombin till recently have been the focus of a variety of anticoagulant strategies, e.g., Claeson, G., "Synthetic Peptides and Peptidomimetics as Substrates and Inhibitors of Thrombin and Other Proteases in the Blood Coagulation System", Blood Coag. Fibrinol. 5, 411-436 (1994). Several classes of anticoagulants currently used in the clinic are direct or indirect inhibitors of thrombin (heparin, low-molecular-weight heparin, coumarins, etc.).

A prothrombinase complex, comprising the protein (factor Xa) converts a proenzyme prothrombin into the active thrombin. Factor Xa belongs to a class of serine proteases and is formed from the protein (factor) X due to activation thereof. Unlike thrombin, which acts on a variety of protein substrates and specific receptors, factor Xa evidently acts on a single substrate, namely prothrombin. Since one molecule of factor Xa is able to generate up to 138 molecules of thrombin, direct inhibitors of protein Xa, as inhibitors of formation of thrombin may be used as efficient agents in the anticoagulant strategy. Therefore, it is obvious that agents, which selectively inhibit protein Xa, may be useful as in vitro diagnostic agents, or as therapeutic agents against diseases associated with coagulation.

Polypeptides derived from hematophagous organisms may be efficient and inhibitors of factor Xa. U.S. Pat. No. 4,588,587 describes the anticoagulant activity of the saliva of the Mexican leech, Haementeria officinalis. The active agent of this saliva is the polypeptide factor Xa inhibitor, antistasin (ATS), another potent and highly specific inhibitor of Factor Xa, called tick anticoagulant peptide (TAP), has been isolated from the whole body extract of the soft tick *Ornithidoros moubata*.

Factor Xa inhibitory compounds, which are not polypeptides, have also been prepared, according to: Tidwell, R. R. et al., "Strategies for Anticoagulation With Synthetic Protease Inhibitors. Xa Inhibitors Versus Thrombin Inhibitors", Thromb. Res., 19, 339-349 (1980); Turner, A. D. et al., "p-Amidino Esters as Irreversible Inhibitors of Factor IXa and Xa and Thrombin", Biochemistry, 25, 4929-4935 (1986); Hitomi, Y. et al, "Inhibitory Effect of New Synthetic Protease Inhibitor (FUT-175) on the Coagulation System", Haemostasis, 15, 164-168 (1985); Sturzebecher, J. et al., "Synthetic Inhibitors of Bovine Factor Xa and Thrombin. Comparison of Their Anticoagulant Efficiency", Thromb. Res., 54, 245-252 (1989); Kam, C. M. et al., "Mechanism Based Isocoumarin Inhibitors for Trypsin and Blood Coagulation Serine Proteases: New Anticoagulants", Biochemistry, 27, 2547-2557 (1988); Hauptmann, J. et al., "Conzparisofz of the Anticoagulant and Antithrombotic Effects of Synthetic Thrombin and Factor Xa Inhibitors", Thromb. Haemost., 63, 220-223 (1990); and the like.

Others have reported Factor Xa inhibitors, which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal C(=NH)—NH2 group; WO 97/21437 describes benzimidazole compounds substituted by a basic radical which are connected to a naphthalene group via a straight or branched chain alkylene, —C(=O) or —S(=O)2 bridging group; WO 99/10316 describes compounds having a 4-phenyl-N-alkylamidino-piperidin connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamides.

Still, there exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit protein Xa. Compounds with a higher degree of binding to protein Xa than to thrombin are especially preferable if they have a good bioavailability and/or solubility.

SUMMARY OF THE INVENTION

The first aspect of the invention is represented by compounds of the general formula I

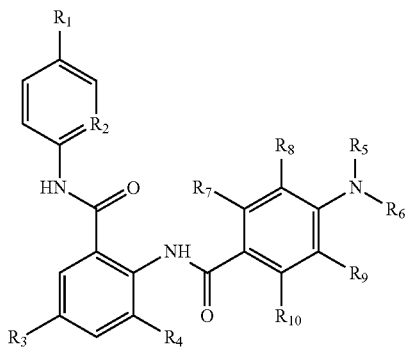

wherein:

$R_1$ is selected from H, —Cl, —F, —Br, —OH, -Me, —OMe;

$R_2$ is selected from CH and N;

$R_3$ and $R_4$ are each independently selected from H, —Cl, —F, —Br, —OH, -Me, —OMe;

$R_5$ is selected from H or $C_1$-$C_6$ alkyl which optionally contains hydroxyl, carboxyl, or ester groups;

$R_6$ is selected from:

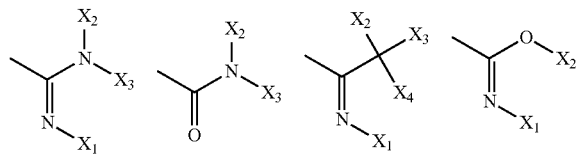

where $X_1$, $X_2$, $X_3$ and $X_4$ are each independently selected from H or $C_1$-$C_6$ alkyl which optionally contains hydroxyl, carboxyl, or ester groups;

$R_8$, $R_9$ and $R_{10}$ are each independently selected from H, —Cl, —F, —Br, —OH, -Me, —OMe;

$R_7$ is selected from H, —Cl, —F, —Br, —OH, -Me, —OMe or:

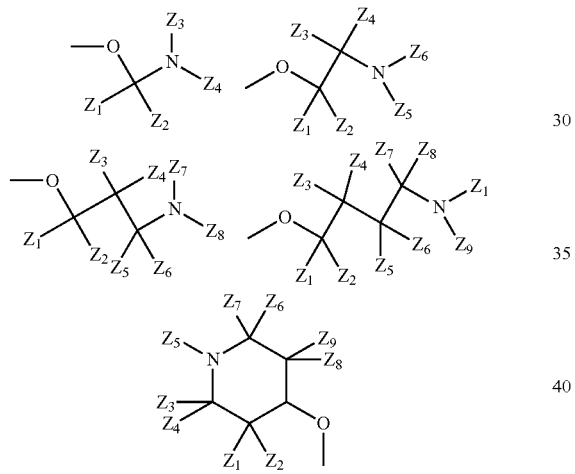

where $Z_1$, $Z_2$, $Z_3$, $Z_4$, $Z_5$, $Z_6$, $Z_7$, $Z_8$, $Z_9$ and $Z_{10}$ are each independently H or $C_1$-$C_6$ alkyl which optionally contains hydroxyl, carboxyl, or ester group;

or a pharmaceutically acceptable isomer, salt, hydrate, solvate and prodrug derivative thereof.

Especially preferable are compounds selected from the group consisting of:

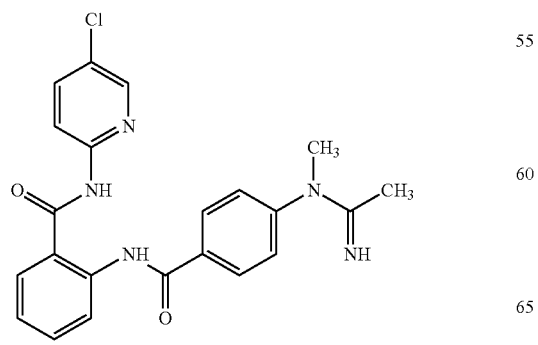

-continued

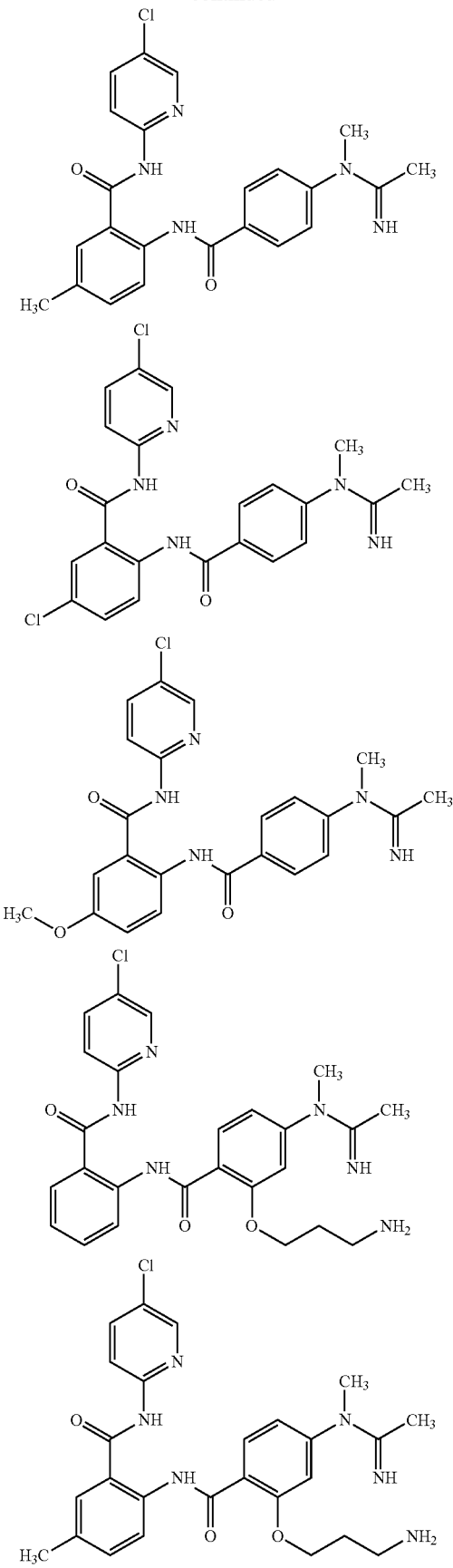

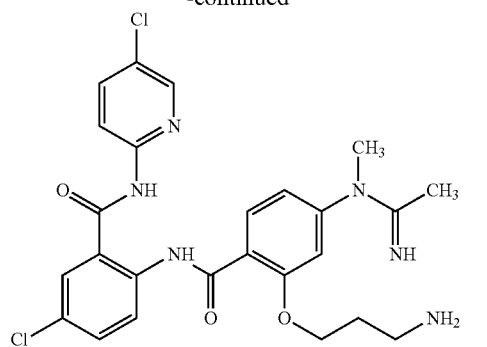
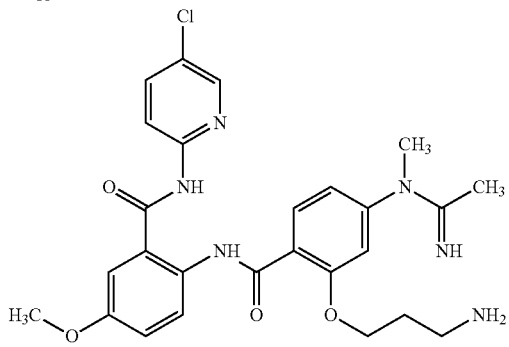
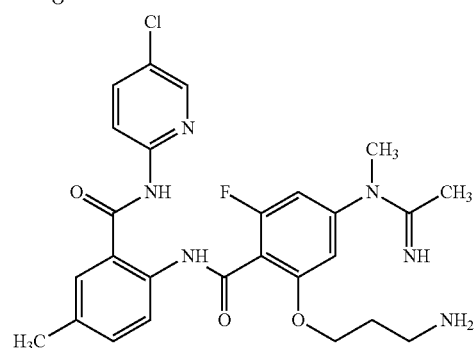
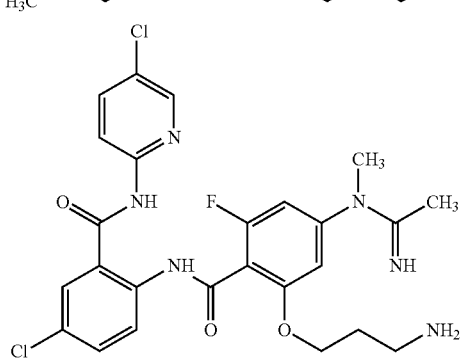
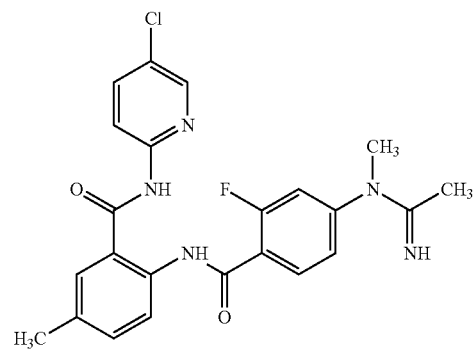
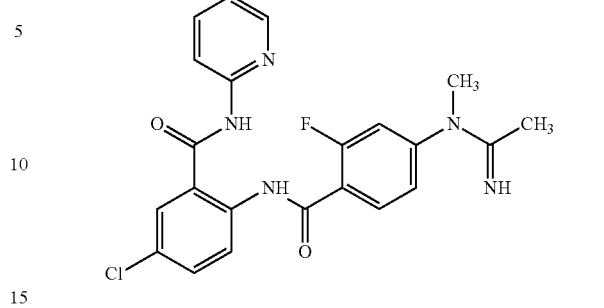
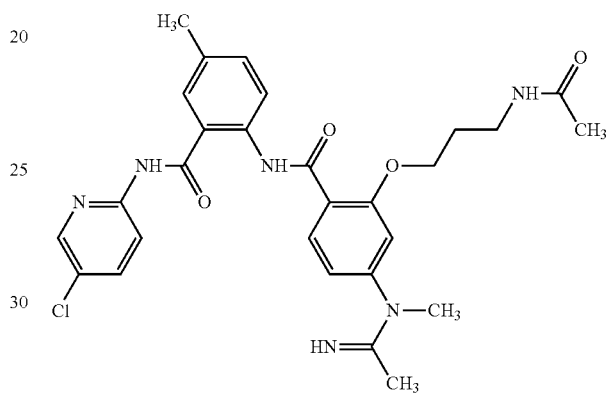
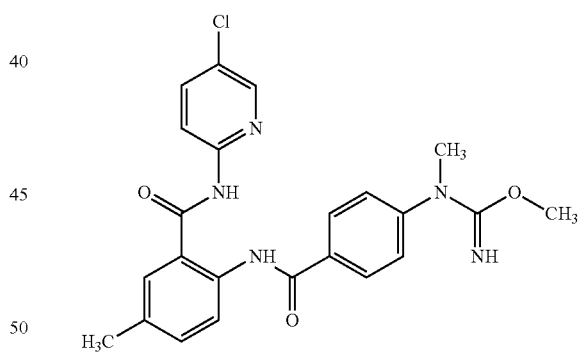
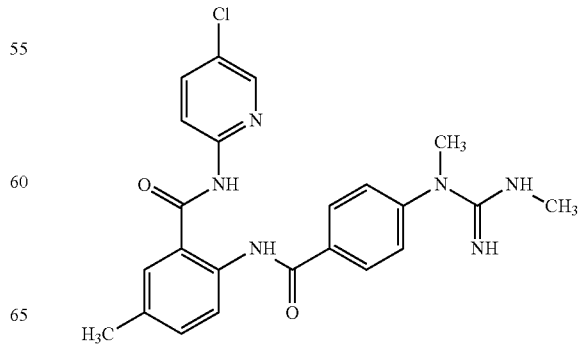

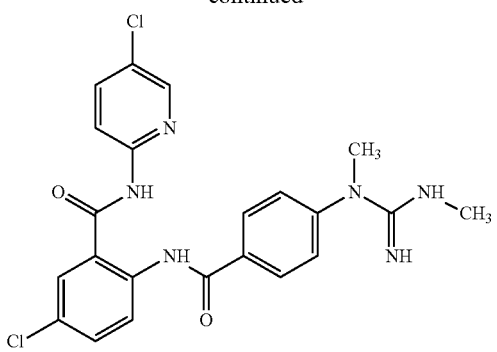

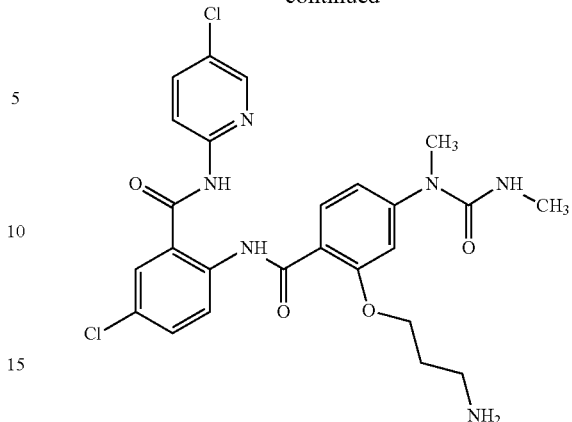

Another aspect of the invention is represented by a pharmaceutical composition for preventing or treating a condition in a mammal characterized by undesired thrombosis comprising a therapeutically effective amount of a compound of the invention.

Besides the active ingredient, which is a compound of the general formula (I), the pharmaceutical composition further comprises a pharmaceutically acceptable carrier, a solvent, or diluent, which may the agents reported in Remington's "The Science and Practice of Pharmacy", Kirk's Othmer's "Encyclopedia of Chemical Technology", and the monography "The Pharmacological Basis of Therapeutics, $3^{rd}$ Edition).

One more aspect of the invention is represented by a method for preventing or treating a condition in a mammal characterized by undesired thrombosis comprising administering atherapeutically effective amount of a compound of formula (I). Conditions in a mammal characterized by undesired thrombosis are well known, in particular: acute coronary syndrome, myocardial infarction, unstable angina, refractory angina, thromboses associated with post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with fitting of prosthetic devices.

And yet one more aspect of the invention is represented by a method for inhibiting the coagulation of a biological sample comprising the step of administering a compound of formula (I).

DETAILED DESCRIPTION OF THE PREFERRED EMBODIMENTS

Synthesis of Chemical Compounds

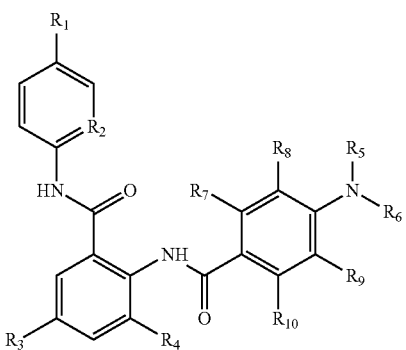

I

Compounds of the general formula (I) can be synthesized by any appropriate method, for example by coupling of corresponding amine (II) with corresponding carboxylic acids derivatives (III)

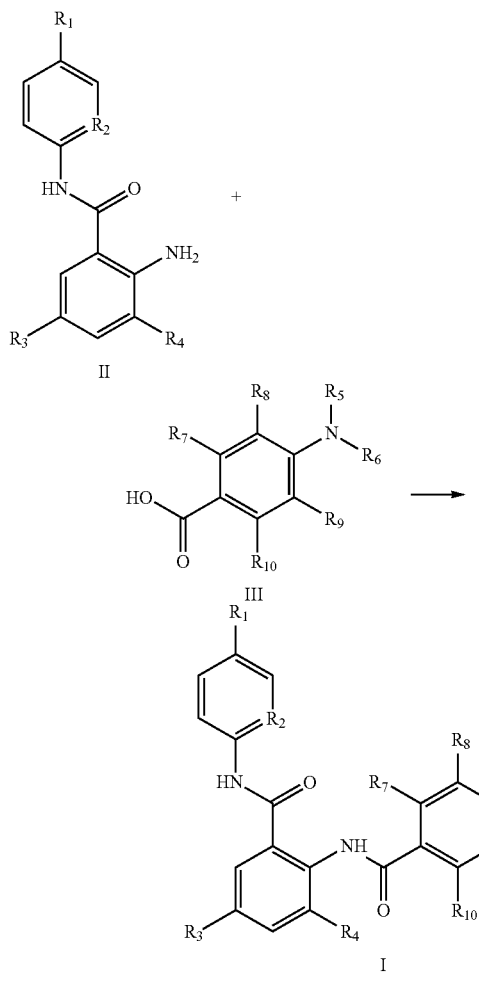

in the presence of appropriate coupling agents, such as 1,1'-Carbonyldiimidazole (CDI), Dicyclohexylcarbodiimide (DCC), N-(3-Dimethylaminopropyl)-N'-ethylcarbodiimide hydrochloride (EDCI) or other appropriate coupling agents. Formation of the amide bond can be also achieved by reaction of chloroanhydrides (IV) and amines (II). Chloroanhydrides (IV) can be obtained from corresponding carboxylic acids (III) by treatment with appropriate reagents such as $SOCl_2$ or $POCl_3$.

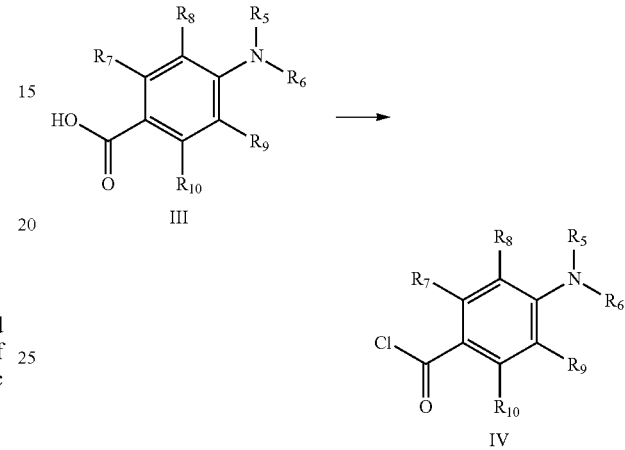

Corresponding carboxylic acids chloroanhydride (IV) easily reacts with amines (II) to yield target compounds (I).

Amines (II) can be obtained by reduction of corresponding nitrocompounds (V) under appropriate conditions. As a reduction agent, for example, $SnCl_2$ or catalytic hydration on Ni-Raney can be used.

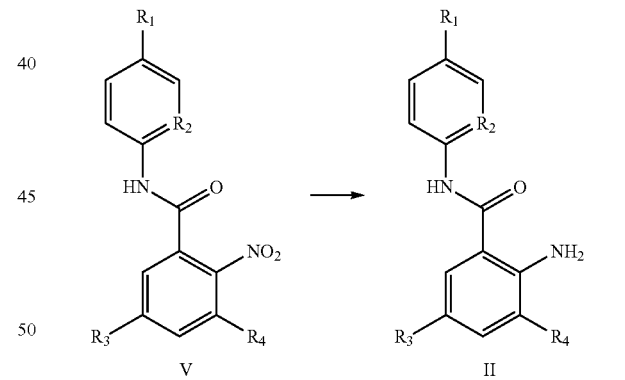

Nitrocompounds (V) can be synthesized from corresponding amines (VI) and nitro-substituted carboxylic acids (VII)

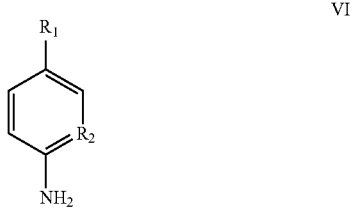

-continued

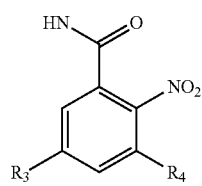
VII

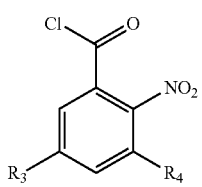
VIII

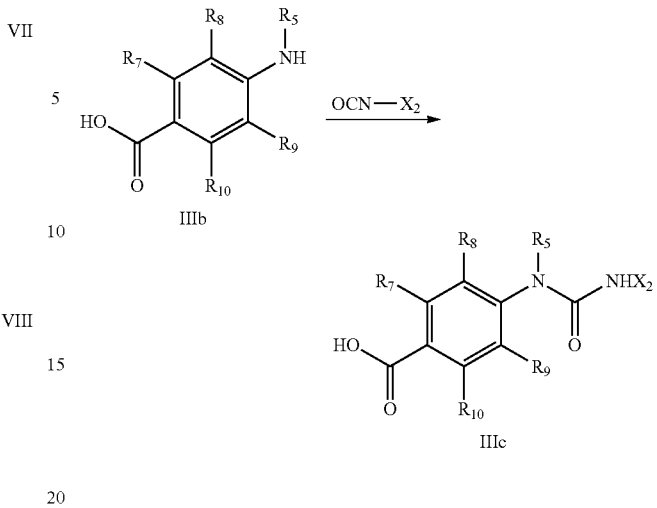

Generally, carboxylic acids (VII) are transformed into corresponding chloroanhydrides (VIII) by treatment with proper reagent such as $SOCl_2$ or $POCl_3$. Chloroanhydrides (VIII) are then smoothly reacts with amines (VI) to yield nitrocompounds (V). An alternative method of synthesis of the amide bond may be a reaction of carboxylic acid (VII) with amine (VI) in the present of appropriate coupling agents, such as DCC, EDCI, and CDI.

In most cases, the above-mentioned reactions proceeds quite smoothly with good yields. However for some radicals $R_5$ and $R_6$ substituted carboxylic acids (III) do not react with amines (II). In these cases appropriate protective group should be used for smooth formation of amide bond and corresponding groups $R_5$ and $R_6$ should be introduced into the molecule after amide bond formation.

Urea derivatives of carboxylic acids (IIIa), can be synthesized by treatment of corresponding methyl or ethyl aminoesters (XI) with CDI followed by amine $X_2X_3NH$. Ethyl or methyl esters are then hydrolyzed in an alkaline medium to give desired compounds:

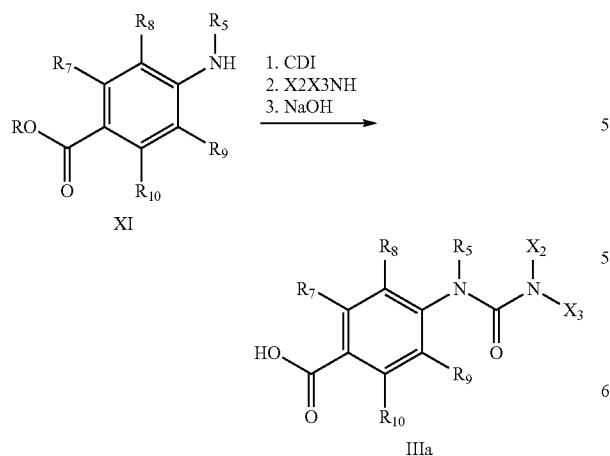

In an alternative way, aminoacid (IIIb) can be transformed into corresponding urea derivatives IIIc by reaction with isocyanates or sodium cyanate in the case of $X_2$=H.

It should be noted that in the case of $X_2$=H, the corresponding urea derivative (IIIc) doesn't react with amine (II) in the presence of DCC, CDI, and EDCI; so there is a need at first to synthesize the protected amine (Ia), with the protective group Y.

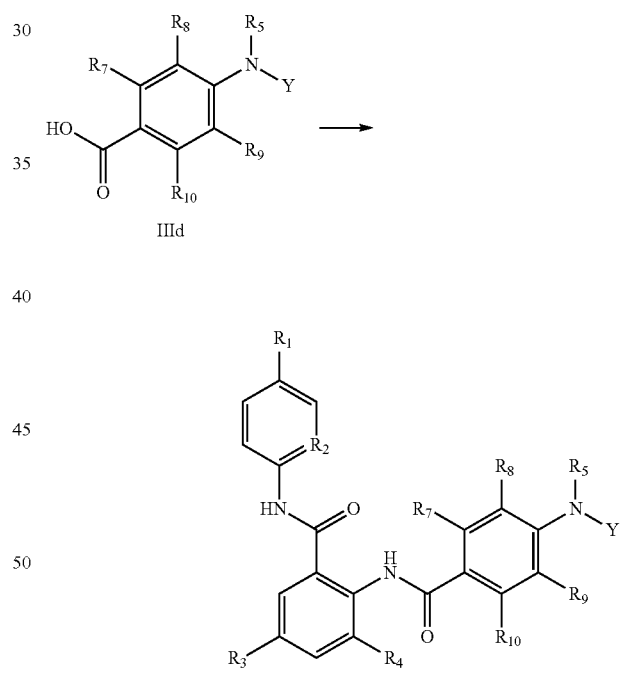

As a protective group, for example, trifluoroacetyl group can be used. Protected amine (Ia) can be synthesized from the corresponding protected aminoacid (IIId) by coupling with amine (II) in the presence of appropriate coupling agent. The protective group then should be removed by appropriate agents; in the case of trifluoroacetyl group, NaOH can be used for this purpose. The amine (Ib) then can be transformed into the corresponding urea derivatives (Ic)

by appropriate method. For example, by consecutive treatment of amine (Ib) with CDI and amine $X_2X_3NH$ or, in the case $X_3=H$, by treatment with a corresponding isocyanate $OCN-Z_2$.

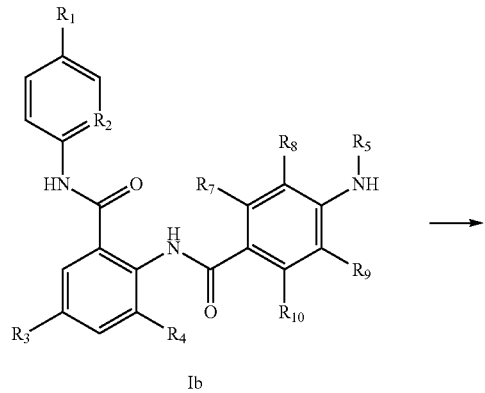

Ib

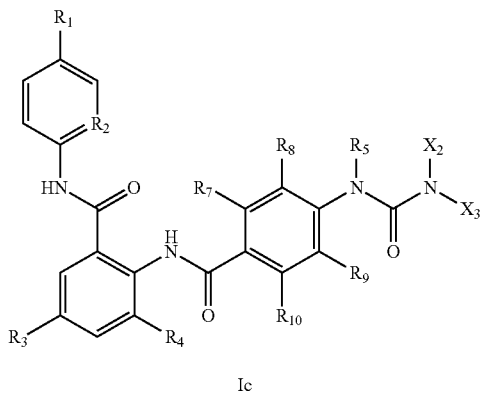

Ic

The amine (Ib) can be also transformed into amidine (Id) by reaction with nitrile $NC-CZ_2Z_3Z_4$ in the presence of dry gaseous HCl. The aminine (Id) can be further alkylated or arylated to amidine (Ie) by appropriate alkyl- or aryl halogenide $X_1$-Hal or other appropriate leaving group contained reagent.

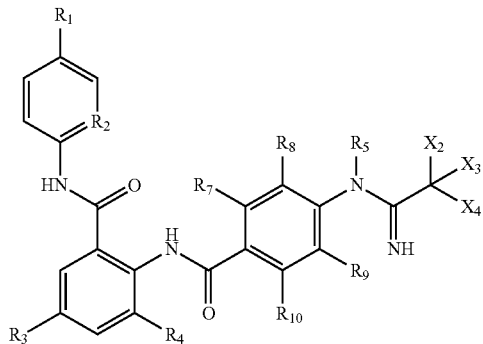

Id

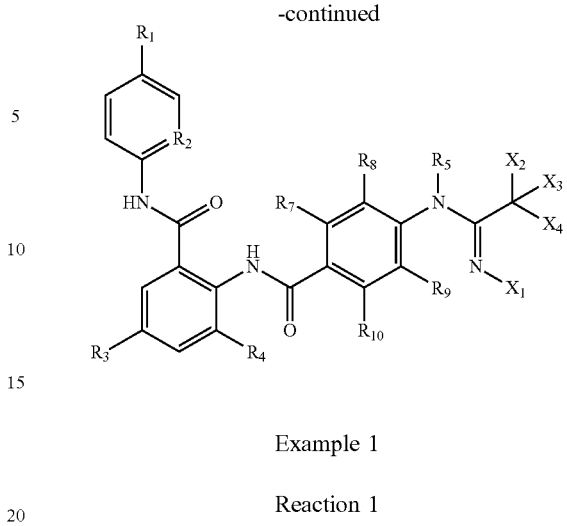

Example 1

Reaction 1

1.9 g of 2-Nitrobenzoic acid is boiled in 20 ml of $SOCl_2$ with a reflux condenser equipped with calcium chloride tube for 4 hours; the obtained solution is cooled, evaporated in a rotary evaporator, twice reevaporated with anhydrous THF; the residue is dissolved in 10 ml of THF; the obtained solution is added dropwise for 30 min to a stirred solution of 1.5 g of 2-Amino-5-chloropyridine in 20 ml of THF. In 15 hours, the reaction mixture is evaporated; the residue is dissolved in 30 ml of chloroform, rinsed with a saturated aqueous solution of $NaHCO_3$; the chloroform extract is evaporated; the residue is applied on a 40×150 mm column filled with 30 to 50 μm of silica gel. The product is eluted with chloroform. Detection is carried out with the aid of an UV-unit at a wavelength of 280 nm. The UV absorbing fractions are collected; the purity of the product is controlled with a thin-layer chromatography technique in chloroform. The $R_f$ of the product is 0.4; the $R_f$ of the starting 2-amino-5-chloropyridine is 0.7. The 2-Nitrobenzoic acid in chloroform remains at the start ($R_f$<0.1). The yield of N-(5-chloropyridine-2-yl)-2-nitrobenzamide is 2.4 g. The mass spectrum (MALDI-VP): M+H 278, M+Na 300.

Reaction 2

1.5 g of N-(5-chloropyridine-2-yl)-2-nitrobenzamide is dissolved in 20 ml of ethylacetate and mixed with a solution of 4 g of $SnCl_2$ in 20 ml of water acidified with 0.3 ml of concentrated HCl. The reaction mixture is stirred vigorously for 1 hour, heated up to boiling, and is boiled for another 3 hours. Then the reaction mixture is filtered, the aqueous fraction is extracted with $CHCl_3$, and the aqueous fraction is added with 30 ml of 10% of aqueous ammonia solution with stirring, and is allowed to stand for a night to precipitate. The next day, the precipitate is filtered and is rinsed with water and chloroform. The aqueous fraction is extracted with chloroform; the extracts are joined together and evaporated. The residue is applied on a 30×150 mm column filled with 40 to 60 μm of silica gel. The product is eluted with chloroform. Detection is carried out with the aid of an UV-unit at a wavelength of 280 nm; the purity of the product is controlled with a thin-layer chromatography technique in chloroform. The $R_f$ of the product is 0.6; the yield of 2-amino-N-(5-chloropyridine-2-yl)benzamide is 650 mg. The mass spectrum (MALDI-VP): M+H 248, M+Na 270.

Reaction 3

1 g of 4-Methylaminobenzoic acid is mixed on cooling with 3 ml of trifluoroacetic anhydride. In 2 hours, the reaction mixture is evaporated and reevaporated with chloroform. The residue is dissolved in chloroform and is applied on a 35×150 mm column filled with 40 to 60 μm of silica gel. The by-products are eluted with chloroform and the target product is eluted with a 9:1 chloroform/isopropanol mixture added with a 1% acetic acid. The yield of 4-methylaminobenzoic acid is 700 mg. $R_f$ is 0.2-0.4. The mass spectrum (MALDI-VP) in negative ions: M−1 246.

Reaction 4

3000 mg of 2-amino-N-(5-chloropyridine-2-yl)benzamide, 250 mg of trifluoroacetate of 4-methylaminobenzoic acid, and 250 mg of EDCI are mixed with 1 ml of THF and stirred for 3 days. Then the mixture is evaporated and applied on a 25×150 mm column filled with 40 to 60 μm of silica gel. The product is eluted with chloroform; $R_f$=0.5. The yield of N-(5-chloropyridine-2-yl)-2-[(4-methyl(trifluoroacetyl)aminophenylcarbonyl)amino]benzamide is 430 mg. The mass spectrum (MALDI-VP): M+H 477, M+Na 499.

Reaction 5

400 mg of N-(5-chloropyridine-2-yl)-2-[(4-methyl-(trifluoroacetyl)aminophenylcarbonyl)-amino]benzamide is dissolved in 5 ml of isopropanol and added with 2 ml of 10% NaOH. The reaction mixture is stirred for 3 hours; then the excess alkali is neutralized with a 5% aqueous solution of HCl; the reaction mixture is evaporated and applied on a 25×150 mm column filled with 40 to 60 μm of silica gel. The product is eluted with chloroform; $R_f$=0.4. The yield of N-(5-chloropyridine-2-yl)-2-[(4-methylaminophenylcarbonyl)amino]benzamide is 320 mg. The mass spectrum (MALDI-VP): M+H 381, M+Na 403.

Reaction 6

300 mg of N-(5-chloropyridine-2-yl)-2-[(4-methylaminophenylcarbonyl)amino]benzamide is dissolved with heating in 5 ml of acetonitrile. The obtained solution is cooled on ice and then a dry gaseous HCl is passed therethrough. In 30 min the solution is placed in a refrigerator and allowed to stand at 5° C. for 48 hours. Then the reaction mixture is added with NaHCO$_3$ with stirring vigorously. New portions of NaHCO$_3$ are added until emission of gases ceases. Usually the procedure requires about 0.5 g of NaHCO$_3$. The solution obtained upon neutralizing the excess with HCl is diluted with 5 ml of water and extracted with chloroform three times. The chloroform extracts are joined together and evaporated. The residue is dissolved in water and applied on a 20×250 mm column filled with reversed phase of C2 (RP2). The column is rinsed with 100 ml of water; then, the elution with a gradient of ethyl alcohol of from 0 to 50% is carried out against a background of 1% acetic acid. The yield of the product is about per 30% of ethyl alcohol. The purity control is carried out with a TLC technique in a 9:1 dioxane/aqueous ammonia system; $R_f$=0.2. The yield of N-(5-chloropyridine-2-yl)-2-[(4-ethaneimidoyl-methylaminophenylcarbonyl)amino]benzamide is 200 mg. The mass spectrum (MALDI-VP): M+H 422, M+Na 444.

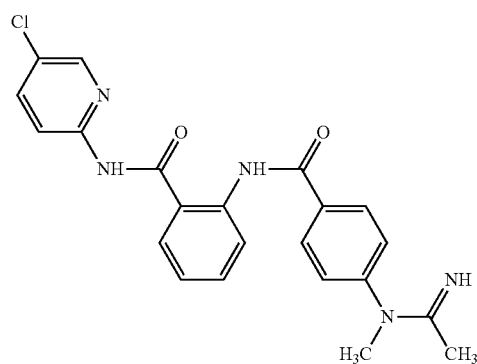 [SMILES: CC(=N)N(C)c1ccc(C(=O)Nc2ccccc2C(=O)Nc2ccc(Cl)cn2)cc1]

Example 2

By analogy with Example 1, in accordance with the procedure described in Example 1 for reaction 1, 800 mg of 5-methyl-2-nitrobenzoic acid yields 650 mg of N-(5-chloropyridine-2-yl)-5-methyl-2-nitrobenzamide. $R_f$=0.45 (chloroform). The mass spectrum (MALDI-VP): M+H 292, M+Na 314.

In accordance with the procedure described in Example 1 for reaction 2, 600 mg of N-(5-chloropyridine-2-yl)-5-methyl-2-nitrobenzamide yields 350 mg of 2-amino-N-(5-chloropyridine-2-yl)-5-methylbenzamide. $R_f$=0.65 (chloroform). The mass spectrum (MALDI-VP): M+H 262, M+Na 284.

In accordance with the procedure described in Example 1 for reaction 4, 300 mg of 2-amino-N-(5-chloropyridine-2-yl)-5-methylbenzamide and 250 mg of trifluoroacetate of 4-methylaminobenzoic acid yields 430 mg of N-(5-chloropyridine-2-yl)-2-[(4-methyl(trifluoroacetyl)aminophenylcarbonyl)amino]-5-methyl-benzamide. $R_f$=0.55 (chloroform). The mass spectrum in positively charged ions m+H 491.

Removal of trifluoroacetyl is carried out in accordance with the procedure described in Example 1 in reaction 5. 400 mg of N-(5-chloropyridine-2-yl)-2-[(4-methyl(trifluoroacetyl)aminophenylcarbonyl)-amino]-5-methyl-benzamide yields 300 mg N-(5-chloropyridine-2-yl)-2-[(4-methylaminophenylcarbonyl)amino]5-methylbenzamide. $R_f$=0.5 (chloroform). The mass spectrum (MALDI-VP): M+H 395, M+Na 417.

The synthesis of amidine is carried out in accordance with the procedure described in Example 1 for reaction 6. The reaction involves 250 mg of N-(5-chloropyridine-2-yl)-2-[(4-methylaminophenylcarbonyl)-amino]-5-methylbenzamide. The reaction yields 130 mg of N-(5-chloropyridine-2-yl)-2-[(4-ethaneimidoyl-methyl-aminophenylcarbonyl) amino]5-methylbenzamide. TLC in a 9:1 dioxane/aqueous ammonia system. $R_f$=0.2 (chloroform). The mass spectrum (MALDI-VP): M+H 436, M+Na 458.

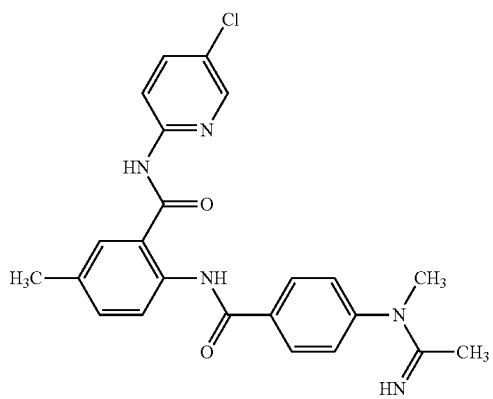 [SMILES: CC(=N)N(C)c1ccc(C(=O)Nc2ccc(C)cc2C(=O)Nc2ccc(Cl)cn2)cc1]

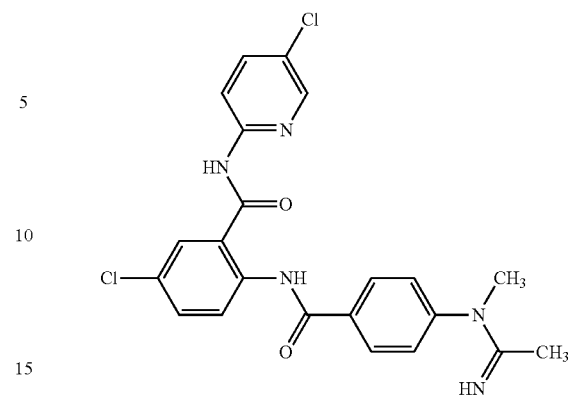

Example 3

By analogy with Example 1, in accordance with the procedure described in Example 1 for reaction 1, 900 mg of 5-chloro-2-nitrobenzoic acid yields 750 mg of N-(5-chloropyridine-2-yl)-5-chloro-2-nitrobenzamide. $R_f$=0.3 (chloroform). The mass spectrum (MALDI-VP): M+H 312, M+Na 334.

In accordance with the procedure described in Example 1 for reaction 2, 700 mg of N-(5-chloropyridine-2-yl)-5-chloro-2-nitrobenzamide yields 350 mg of 2-amino-N-(5-chloropyridine-2-yl)-5-chlorobenzamide. $R_f$=0.6 (chloroform). The mass spectrum (MALDI-VP): M+H 282, M+Na 304.

In accordance with the procedure described in Example 1 for reaction 4, 300 mg of 2-amino-N-(5-chloropyridine-2-yl)-5-chlorobenzamide and 250 mg of trifluoroacetate of 4-methylaminobenzoic acid yields 430 mg of N-(5-chloropyridine-2-yl)-2-[(4-methyl(trifluoroacetyl)aminophenylcarbonyl)amino]-5-chloro-benzamide. $R_f$=0.5 (chloroform). The mass spectrum (MALDI-VP): M+H 511, M+Na 533.

Removal of trifluoroacetyl is carried out in accordance with the procedure described in Example 1 for reaction 5. 400 mg of N-(5-chloropyridine-2-yl)-2-[(4-methyl(trifluoroacetyl)aminophenylcarbonyl)amino]-5-chloro-benzamide yields 300 mg N-(5-chloropyridine-2-yl)-2-[(4-methylaminophenylcarbonyl)amino]-5-chlorobenzamide. $R_f$=0.45 (chloroform). The mass spectrum (MALDI-VP): M+H 415, M+Na 437.

The synthesis of amidine is carried out in accordance with the procedure described in Example 1 for reaction 6. The reaction involves 250 mg of N-(5-chloropyridine-2-yl)-2-[(4-methylaminophenylcarbonyl)-amino]-5-chlorobenzamide. The reaction yields 130 mg of N-(5-chloropyridine-2-yl)-2-[(4-ethaneimidoyl-methyl-aminophenylcarbonyl)amino]-5-chlorobenzamide. $R_f$=0.2 (9:1 dioxane/aqueous ammonia). The mass spectrum (MALDI-VP): M+H 456, M+Na 478.

Example 4

By analogy with Example 1, in accordance with the procedure described in Example 1 for reaction 1, 1.5 g of 5-methoxy-2-nitrobenzoic acid yields 1.1 g of N-(5-chloropyridine-2-yl)-5-methoxy-2-nitrobenzamide. $R_f$=0.5 (chloroform). The mass spectrum (MALDI-VP): M+H 308, M+Na 330.

In accordance with the procedure described in Example 1 for reaction 2, 1 g of N-(5-chloropyridine-2-yl)-5-methoxy-2-nitrobenzamide yields 300 mg of 2-amino-N-(5-chloropyridine-2-yl)-5-methoxybenzamide. $R_f$=0.7 (chloroform). The mass spectrum (MALDI-VP): M+H 278, M+Na 300.

In accordance with the procedure described in Example 1 for reaction 4, 250 mg of 2-amino-N-(5-chloropyridine-2-yl)-5-methoxybenzamide and 220 mg of trifluoroacetate of 4-methylaminobenzoic acid yields 310 mg of N-(5-chloropyridine-2-yl)-2-[(4-methyl(trifluoroacetyl)aminophenylcarbonyl)amino]-5-methoxybenzamide. $R_f$=0.6 (chloroform). The mass spectrum (MALDI-VP): M+H 507, M+Na 529.

Removal of trifluoroacetyl is carried out in accordance with the procedure described in Example 1 in reaction 5. 280 mg of N-(5-chloropyridine-2-yl)-2-[(4-methyl(trifluoroacetyl)aminophenylcarbonyl)-amino]-5-methoxybenzamide yields 200 mg N-(5-chloropyridine-2-yl)-2-[(4-methylaminophenylcarbonyl)amino]5-methoxybenzamide. $R_f$=0.5 (chloroform). The mass spectrum (MALDI-VP): M+H 411, M+Na 433.

The synthesis of amidine is carried out in accordance with the procedure described in Example 1 for reaction 6. The reaction involves 170 mg of N-(5-chloropyridine-2-yl)-2-[(4-methylaminophenylcarbonyl)-amino]-5-methoxybenzamide. The reaction yields 110 mg of N-(5-chloropyridine-2-yl)-2-[(4-ethaneimidoyl-methyl-aminophenylcarbonyl)amino]5-methoxybenzamide. $R_f$=0.2 (9:1 dioxane/aqueous ammonia). The mass spectrum (MALDI-VP): M+H 452, M+Na 474.

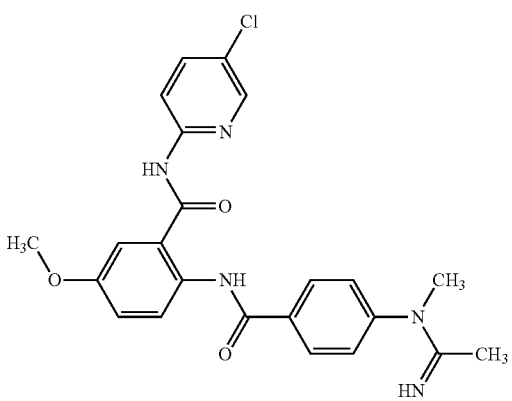 [SMILES: COc1ccc(NC(=O)c2ccc(N(C)C(C)=N)cc2)c(C(=O)Nc2ccc(Cl)cn2)c1]

Example 5

Reaction 1

1 g of aminosalicylic acid is dissolved in 20 ml of aqueous dioxane. The solution is added with 900 mg of di-tertbutyl-dicarbonate and 3 ml of 10% aqueous solution of NaOH. In 24 hours, the reaction mixture is evaporated, the 4-tertbutoxycarbonylaminosalicylic acid is purified by recrustallixation from ethanol. The yield is 1.1 g.

Reaction 2

A mixture of 0.5 g of 4-tertbutoxycarbonylaminosalicylic acid, 0.6 g of N-(3-chloropropyl)-acetamide, and 0.5 g of $K_2CO_3$ is heated to 110° C.; in an hour, the reaction mixture is cooled, diluted with water, and extracted with chloroform; the extract is evaporated and is applied onto a 30×150 mm column filled with 40- to 60 nm of silica gel; the product is eluted with a 9:1 chloroform/ethanol mixture. $R_f$=0.5 (9:1 chloroform/ethanol). The yield of 2-[3-(acetylamino)propoxy]-4-[(tertbutoxycarbonyl)amino]benzoic acid is 400 mg.

Reaction 3

370 mg of 2-[3-(acetylamino)propoxy]-4-[(tertbutoxycarbonyl)amino]benzoic acid is dissolved in 3 ml of ethanol and added with 100 μl of 10% HCl. In 2 hours, the reaction mixture is evaporated and the product is purified by recrystallization from ethanol. $R_f$=0.45 (9:1 chloroform/ethanol). The yield of 2-[3-(acetylamino)propoxy]-4-aminobenzoic acid is 300 mg.

Reaction 4

270 mg of 2-[3-(acetylamino)propoxy]-4-aminobenzoic acid is mixed with 300 μl of 40% formaldehyde, a solution of 400 mg of NaOH in 2 ml of water, and 400 mg of a zinc powder. The reaction mixture is stirred and is allowed to stand at 60° C. for 4 hours; then it is filtered, the precipitate is rinsed with aqueous ethanol; the filtrate is acidified with aqueous HCl up to pH 4-5, evaporated, and the residue is applied onto a 25×150 mm column filled with 40 to 60 μm of silica gel. The product is eluted in a 9:1 chloroform/ethanol system. $R_f$=0.5. The yield of 2-[3-(acetylamino)propoxy]-4-methylamino)benzoic acid is 150 mg.

Reaction 5

130 mg of 2-[3-(acetylamino)propoxy]-4-methylamino)benzoic acid is dissolved in 2 ml of aqueous ethanol containing 500 mg of NaOH. The mixture is sealed into an ampoule, which is heated up to 100° C. for 10 hours. The ampoule is cooled, opened, and the excess alkali is neutralized to pH 8-9 of the diluted HCl; then the obtained solution is evaporated. The residue is applied onto a 20×150 column filled with 40 to 60 μm of silica gel. The product is eluted with chloroform. $R_f$=0.3. The yield of 2-[3-aminopropoxy]-4-(methylamino)benzoic acid is 100 mg.

Reaction 6

90 mg of 2-[3-aminopropoxy]-4-(methylamino)benzoic acid is mixed with 1 ml of trifluoroacetic anhydride. In 1 hour, the reaction mixture is evaporated, the residue is applied onto a 20×150 column filled with 40 to 60 μm of silica gel. The product is eluted in a 9:1 chloroform/ethanol system. The yield of 2-[3-(trifluoroacetylamino)propoxy]-4-[trifluoroacetyl-(methyl)amino]benzoic acid is 100 mg.

Reaction 7

80 mg of 2-amino-N-(5-chloropyridinw-2-yl)benzamide, 100 mg of 2-[3-(trifluoroacetylamino)propoxy]-4-[trifluoroacetyl-(methyl)amino]benzoic acid and 80 mg of EDCI are mixed in 1 ml of THF and are being stirred for 48 hours. Then the reaction mixture is evaporated, the residue is applied onto a column with silica gel and the product is eluted with methylene chloride. $R_f$=0.5 (methylene chloride). The yield of N-(5-chloropyridine-2-yl)-2-{4-trifluoroacetyl(methyl)amino]-2-[3-(trifluoroacetylamino)propoxy]phenylcarbonylamino}benzamide is 80 mg.

Reaction 8

70 mg of N-(5-chloropyridine-2-yl)-2-{4-trifluoroacetyl(methyl)amino]-2-[3-(trifluoroacetylamino)propoxy]phenylcarbonylamino}benzamide are dissolved in a mixture of 100 μl of 3M NaOH and 1 ml of ethanol and stirred for 1 hour; then the solution is neutralized, the residue is evaporated, the product is purified with a chromatography technique on silica gel. The product is eluted with methylene chloride. $R_f$=0.4. The yield of N-(5-chloropyridine-2-yl)-2-[4-methylamino-2-(3-aminopropoxy)-phenylcarbonylamino]-benzamide is 55 mg.

Reaction 9

50 mg of N-(5-chloropyridine-2-yl)-2-[4-methylamino-2-(3-aminopropoxy)-phenylcarbonylamino]benzamide are dissolved on heating in 2 ml of acetonitrile. The obtained solution is cooled on ice and then a dry gaseous HCl is passed therethrough. In 30 min, the solution is placed in a refrigerator and allowed to stand at 5° C. for 48 hours. Then, the reaction mixture is added with $NaHCO_3$ and stirred thoroughly. New portions of $NaHCO_3$ are added till the emission of gases ceases. The solution obtained after neutralization of the excess HCl is diluted with 5 ml of water and extracted three times with chloroform. The chloroform-treated extracts are evaporated. The residue is dissolved in water and titrated with a 1% aqueous NaOH till pH 9. The solution is allowed to stand at 25° C. for 3 hours; then it is neutralized, evaporated, the residue is applied onto a 20×250 column filled with a reversed phase C2 (RP2). The column is washed with 100 ml of water; then the elution is carried out with a gradient of ethyl alcohol from 0 to 50% against the background of a 1% aqueous acetic acid. The product yields per approximately 30% or ethyl alcohol. The purity control is carried out with a TLC technique in a 8:2 isopropanol/aqueous ammonia system. $R_f$=0.5. The yield of N-(5-chloropyridine-2-yl)-2-[4-(ethaneimidoylmethyl-amino)-2-(3-aminopropoxy)phenylcarbonyl-amino]benz-amide is 20 mg. The mass spectrum (MALDI-VP): M+H 495, M+Na 517.

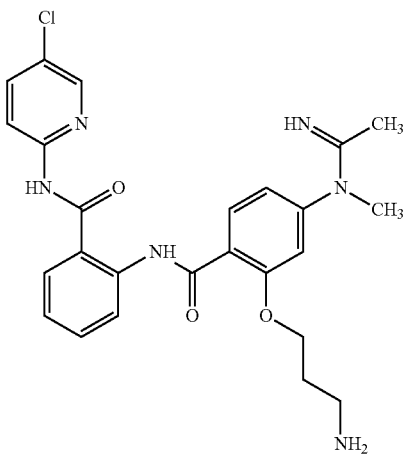 [SMILES: CC(=N)N(C)c1ccc(C(=O)Nc2ccccc2C(=O)Nc2ccc(Cl)cn2)c(OCCCN)c1]

Example 6

Reaction 1

95 mg of 2-amino-N-(5-chloropyridine-2-yl)-5-methyl-benzamide, 120 mg of 2-[3-(trifluoroacetylamino)-propoxy]-4-[trifluoroacetyl(methyl)amino]benzoic acid, and 80 mg of EDCI are mixed with 1 ml of THF and stirred for 48 hours. Then the reaction mixture is evaporated, the residue is applied onto a column with silica gel and the product is eluted with methylene chloride. $R_f$=0.5. The yield of N-(5-chloropyridine-2-yl)-2-[4-(trifluoroacetyl(methyl)amino-2-(3-trifluoroacetylamino)propoxy)phenylcarbo-nylamino]-5-methylbenzamide is 85 mg.

Reaction 2

80 mg of N-(chloropyridine-2-yl)-2-[4-(trifluoroacetylm-ethyl)amino)2-(3-(trifluoroacetylamino)-propoxy)phenyl-carbonylamino]-5-methylbenzamide are dissolved in a mixture of 100 µl of 3M of aqueous NaOH and 1 ml of ethanol and stirred for 1 hour; then the solution is neutralized and the residue is evaporated; the product is purified with a TLC technique on silica gel. The product is eluted with methyle chloride. $R_f$=0.4. The yield of N-(5-chloropyridine-2-yl)-2-[4-methylamino-2-(3-aminopropoxy)phenylcarbo-nylamino]-5-methylbenzamide is 65 mg.

Reaction 3

60 mg of N-(5-chloropyridine-2-yl)-2-[4-methylamino-2-(3-aminopropoxy)-phenylcarbonylamino]-5-methylbenz-amide are dissolved on heating in 2 ml of acetonitrile. The obtained solution is cooled on ice and a dry gaseous HCl is passed therethrough. In 30 min, the solution is placed in a refrigerator and allowed to stand at 50° C. for 48 hours. Then the reaction mixture is added with NaHCO$_3$ and stirred thoroughly. New portions of NaHCO$_3$ are added till the emission of gases ceases. The solution obtained upon neutralization of the excess HCl is diluted with 5 ml of water and extracted three times with chloroform. The chloroform-treated extracts are joined together and evaporated. The residue is dissolved in water and titrated with a 1% NaOH to pH=9. The solution is allowed to stand at 25° C. for 3 hours, neutralized, evaporated, and the residue is applied onto a 2-×250 column filled with a reversed phase of C2 (RP2). The column is washed with 100 ml of water and then the elution is performed with an ethyl alcohol gradient of from 0 to 50% against the background of 1% aqueous acetic acid. The product yield is approximately per 30% of ethyl alcohol. The purity is controlled with a TLC technique in an 8:2 isopropanol/aqueous ammonia system. $R_f$=0.5. The yield of N-(5-chloropyridine-2-yl)-2-[4-ethaneimidoylmethyl-amino)-2-(3-aminopropoxy)phenylcarbonyl-amino]-5-methyl-benzamide is 30 mg. The mass spectrum (MALDI-VP): M+H 509, M+Na 531.

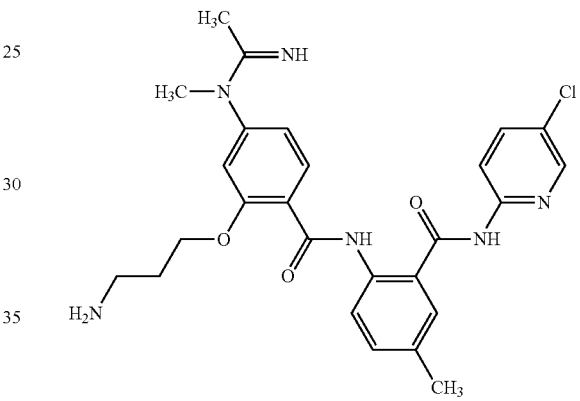

Example 7

Reaction 1

95 mg of 2-amino-N-(5-chloropyridine-2-yl)-5-chlo-robenzamide, 90 mg of 2-[3-(trifluoroacetylamino)propoxy]-4-[trifluoroacetyl(methylamino)benzoic acid, and 80 mg of EDCI are mixed with 1 ml of THF and stirred for 48 hours. Then the reaction mixture is evaporated, the residue is applied onto a column containing silica gel, and the product is eluted with methylene chloride. $R_f$=0.5 (methylene chloride). The yield of N-(5-chloropyridine-2-yl)-2-[4-(trifluoroacetyl(methyl)amino)-2-(3-(trifluoroacety-lamino)-propoxy)phenylcarbonylamino]-5-chlorobenzamide is 85 mg.

Reaction 2

80 mg of N-(5-chloropyridine-2-yl)-2-[4-(trifluoroacetyl-methyl)amino)-2-(3-(trifluoroacetylamino)-propoxy)phe-nylcarbonylamino]-5-chlorobenzamide are dissolved in a mixture of 100 µl of a 3M aqueous NaOH and 1 ml of ethanol and stirred for 1 hour; then the solution is neutralized, the residue is evaporated, and the product is purified with a chromatography technique on silica gel. The product is eluted with methylene chloride. $R_f$=0.4. The yield of N-(5-chloropyridine-2-yl)-2-[4-methylamino-2-(3-(acetylamino)propoxy)phenylcarbonylamino]-5-chlorobenzamide is 65 mg.

60 mg of N-(5-chloropyridine-2-yl)-2-[4-methylamino-2-(3-(acetylamino)propoxy)phenyl-carbonyl-amino]-5-chlorobenzamide are dissolved on heating in 2 ml of acetonitrile. The obtained solution is cooled on ice, and a dry gaseous HCl is passed therethrough. In 30 min, the solution is placed in a refrigerator and is allowed to stand at 5° C. for 48 hours. Then the reaction mixture is added with NaHCO$_3$ and stirred thoroughly. New portions of NaHCO$_3$ are added until the emission of gases ceases. The solution obtained upon neutralization of the excess HCl is diluted with 5 ml of water and is extracted with chloroform three times. The chloroform-treated extracts are joined together and evaporated. The residue is dissolved in water and titrated with a 1% aqueous NaOH till pH=9. The solution is allowed to stand at 25° C. for 3 hour, neutralized, evaporated, and the residue is applied onto a 20×250 column filled with a reversed phase C2 (RP2). The column is washed with 100 ml of water; then elution is performed with a ethyl alcohol gradient of from 0 to 50% against the background of 1% aqueous acetic acid. The product yield is about per 30% of ethyl alcohol. The purity is controlled with a TLC technique in an 8:2 isopropanol/aqueous ammonia system. R$_f$=0.5. The yield of N-(5-chloropyridine-2-yl)-2-[4-(ethaneimidoylmethylamino)-2-(3-aminopropoxy)phenylcarbonylamino]-5-chlorobenzamide is 30 mg. The mass spectrum (MALDI-VP): M+H 528, M+Na 550.

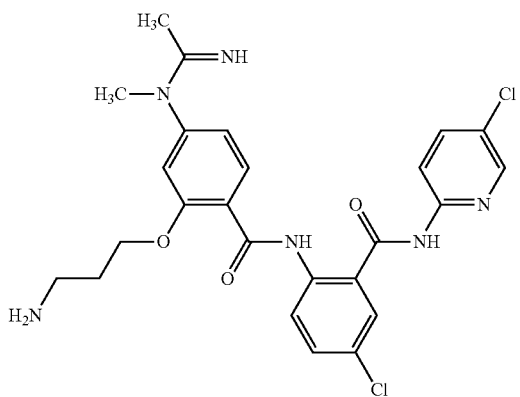 [SMILES: CC(=N)N(C)c1ccc(C(=O)Nc2ccc(Cl)cc2C(=O)Nc2ccc(Cl)cn2)c(OCCCN)c1]

Example 8

Reaction 1

90 mg of 2-amino-N-(5-chloropyridine-2-yl)-5-methoxybenzamide, 100 mg of 2-[3-trifluoroacetylamino)propoxy]-4-[trifluoroacetylmethylamino)]benzoic acid, and 90 mg of EDCI are mixed with 1 ml of THF and stirred for 48 hours. Then the reaction mixture is evaporated, the residue is applied onto a column with silica gel, and the product is eluted with methylene chloride. R$_f$=0.5 (methylene chloride). The yield of N-(5-chloropyridine-2-yl)-2-[4-(trifluoroacetyl(methyl)amino)-2-(3-(trifluoroacetylamino)propoxy)phenylcarbonylamino]-5-methoxybenzamide is 85 mg.

Reaction 2

80 mg of N-(5-chloropyridine-2-yl)-2-[4-(trifluoroacetylmethyl)amino)-2-(3-(trifluoroacetylamino)propoxy)phenyl-carbonylamino]-5-methoxybenzamide are dissolved in a mixture of 100 μl of 3 M aqueous NaOH and 1 ml of ethanol and stirred for 1 hour; then the solution is neutralized, the residue is evaporated, and the product is purified with a chromatographic technique on silica gel. The product is eluted with methylene chloride. R$_f$=0.4. The yield of N-(5-chloropyridine-2-yl)-2-[4-(methylamino-2-(3-aminopropoxy)phenylcarbonylamino]-5-methoxybenzamide is 65 mg.

60 mg of N-(5-chloropyridine-2-yl)-2-[4-(methylamino-2-(3-aminopropoxy)phenylcarbonylamino]-5-methoxybenzamide is dissolved with heating in 2 ml of acetonitrile. The obtained solution is cooled with ice and dry gaseous HCl is passed therethrough. In 30 min, the solution is placed into a refrigerator and allowed to stand at 5° C. for 48 hours. Then the reaction mixture is added with NaHCO$_3$ is added till the gas emission ceases. The solution obtained upon neutralization of excess HCl is dissolved in 5 ml of water and extracted three times with chloroform. The chloroform-treated extracts are joined together and evaporated. The residue is dissolved in water and titrated with 1% aqueous NaOH till pH=9. The solution is allowed to stand at 25° C. for 3 hours; then the solution is neutralized, evaporated, and the residue is applied onto a 20×250 column filled with a reversed phase of C2 (RP2). The column is washed with 100 ml of water, and elution is carried out with a gradient of ethyl alcohol from 0 to 50% against the background of 1% aqueous acetic acid. The yield of the product is about per 30% ethyl alcohol. The purity of the product is controlled with a TLC technique in a 8:2 isopropanol/aqueous ammonia system. R$_f$=0.5. The yield of N-(5-chloropyridine-2-yl)2-[4(ethaneimidoylmethylamino)-2-(3-aminopropoxy)phenylcarbonyl-amino]-5-methoxybenzamide is 30 mg. The mass spectrum (MALDI-VP): M+H 525, M+Na 547.

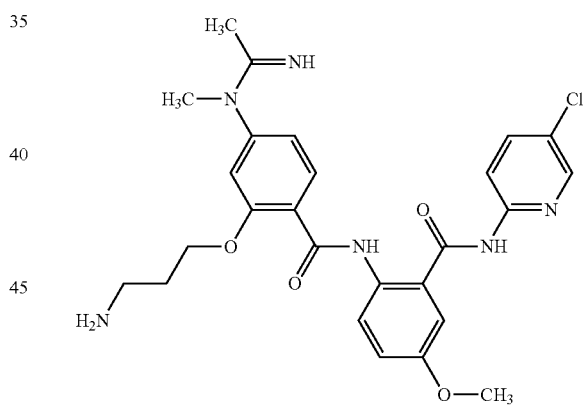

Example 9

Reaction 1

1.5 g of 4-methylamino-6-fluorosalicylic acid is dissolved in 20 ml of aqueous dioxane. The solution is added with 2 g of di-tertbutyldicarbonate and 3 ml of 10% aqueous solution of NaOH. In 24 hours, the reaction mixture is evaporated, the 4-tertbutoxycarbonyl(methylamino)-6-fluorosalicylic acid is purified by recrystallization from ethanol. The yield is 1.6 g.

Reaction 2

A mixture of 1.5 g of 4-4-tertbutoxycarbonyl(methylamino)-6-fluorosalicylic acid, 1.6 g of N-(3-chloropropyl)- trifluoroacetamide, and 1.5 g of $K_2CO_3$ is heated to 110° C.; in 1 hour the reaction mixture is cooled, diluted with water, extracted with chloroform, and the extract is applied onto a 30×150 column filled with 40 to 60 μm of silica gel; the product is eluted with a 9:1 chloroform/ethanol mixture. $R_f$=0.5 (chloroform/ethanol mixture). The yield of 2-[3-(trifluoroacetamino)propoxy]-4-[(tert-butoxycarbonyl) methylamino]-6-fluorobenzoic acid is 390 mg.

Reaction 3

370 mg of 2-[3-(trifluoroacetamino)propoxy]-4-[(tert-butoxycarbonyl)methylamino]-6-fluorobenzoic acid are dissolved in 3 ml of ethanol and added with 100 μl of 10% HCl. In 2 hours the reaction mixture is evaporated, the product is purified by recrystallization from ethanol. $R_f$=0.45 (9:1 chloroform/ethanol). The yield of 2-[3-trifluoroacetylamino)propoxy]-4-methylamino-6-fluorobenzoic acid is 280 mg.

Reaction 4

270 mg of 2-[3-(trifluoroamino)propoxy]-4-methylamino-6-fluorobenzoic acid are mixed with 1 ml of trifluoroacetic anhydride. In 1 hour the reaction mixture is evaporated, the residue is applied onto a 20×150 column filled with 40 to 60 μm of silica gel; the product is eluted with a 9:1 chloroform/ethanol mixture. The yield of 2-[3-(trifluoroacetylamino)propoxy]-4-[trifluoroacetyl-(methyl)amino]-6-fluorobenzoic acid is 280 mg.

Reaction 5

250 mg of 2-amino-N-(5-chloropyridine-2-yl)-5-methylbenzamide, 280 mg of 2-[3-(trifluoroacetylamino)propoxy]-4-[trifluoroacetyl(methyl)amino]-6-fluorobenzoic acid, and 300 mg of EDCI are mixed with 2 ml of THF and stirred for 48 hours. Then the reaction mixture is evaporated, the residue is applied onto a column with silica gel therein, and the product is eluted with methylene chloride. $R_f$=0.5 (methylene chloride). The yield of N-(5-chloropyridine-2-yl)-2-[4-(trifluoroacetyl(methyl)amino)-2-(3-trifluoroacetylamino)propoxy)-6-fluorophenyl carbonylamino]-5-methylbenzamide is 270 mg.

Reaction 6

250 mg of N-(5-chloropyridine-2-yl)-2-[4-(trifluoroacetylmethyl)amino)-2-3-(trifluoroacetylamino)propoxy)-6-fluoroohenylcarbonylamino]-5-methylbenzamide are dissolved in a mixture of 300 μl of 3M aqueous NaOH and 2 ml of ethanol and stirred for 1 hour; then the solution is neutralized, the residue is evaporated, and the product is purified with a chromatographic technique on silica gel. The product is eluted with methylene chloride. $R_f$=0.4. The yield of N-(5-chloropyridine-2-yl)-2-[4-methylamino-2-(3-aminopropoxy)-6-fluorophenylcarbonylamino]-5-methylbenzamide is 160 mg.

Reaction 7

150 mg of N-(5-chloropyridine-2-yl)-2-[4-methylamino-2-(3-aminopropoxy)-6-fluorophenylcarbonylamino]-5-methylbenzamide is dissolved with heating in 5 ml of acetonitrile. The obtained solution is cooled in ice; then a dry gaseous HCl is passed therethrough. In 30 min, the solution is placed in a refrigerator and allowed to stand at 5° C. for 48 hours. The reaction mixture is added with $NaHCO_3$ and stirred thoroughly. New portions of $NaHCO_3$ are added until the emission of gases ceases. The solution obtained upon neutralization of excess HCl is diluted in 10 ml of water and extracted three times with chloroform. The chloroform-treated extracts are joined together and evaporated. The residue is dissolved in water and titrated with 1% aqueous NaOH till pH=9. The solution is allowed to stand at 25° C. for 3 hours, evaporated, and the residue is applied onto a 20×250 column filled with a reversed phase of C2 (FP2). The column is washed with 100 ml of water; then the elution is carried out with an ethyl alcohol gradient of from 0 to 50% against the background of 1% aqueous acetic acid. The product yield is about per 30% of ethyl alcohol. The product purity is controlled with a TLC technique in a 3:5:2 acetonitrile/dioxane/aqueous ammonia system. $R_f$=0.5. The yield of N-(5-chloropyridine-2-yl)-2-[4-(ethaneimidoylmethylamino)-2-(3-aminopropoxy)-6-fluorophenylcarbonylamino]-5-methylbenzamide is 70 mg. The mass spectrum (MALDI-VP): M+H 527, M+Na 549.

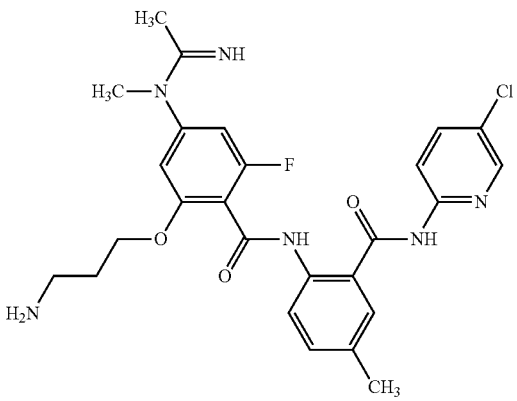 [SMILES: CC(=N)N(C)c1cc(F)c(C(=O)Nc2ccc(C)cc2C(=O)Nc2ccc(Cl)cn2)c(OCCCN)c1]

Example 10

Reaction 1

250 mg of 2-amino-N-(5-chloropyridine-2-yl)-5-chlorobenzamide, 290 mg of 2-[3-(trifluoroacetylamino) propoxy]-4-[trifluoroacetyl(methyl)amino]-6-fluorobenzoic acid, and 280 mg EDCI are mixed with 1 ml of THF and stirred for 48 hours. Then the reaction mixture is evaporated, the residue is applied onto a column filled with silica gel, and the product is eluted with methylene chloride. $R_f$=0.5 (methylene chloride). The yield of N-(5-chloropyridine-2-yl)-2-[4-trifluoroacetyl(methyl)amino-2-(3-(trifluoroacetylamino)propoxy)-6-fluorophenylcamonylamino]-5-chlorobenzamide is 270 mg.

Reaction 2

180 mg of N-(5-chloropyridine-2-yl)-2-[4-trifluoroacetylmethyl)amino-2-(3-trifluoroacetylamino)propoxy)-6-fluorophenylcarbonylamino]-5-chlorobenzamide are dissolved in a mixture of 400 μl of 3M NaOH and 2 ml of ethanol and stirred for 1 hour; then the solution is neutralized, the residue is evaporated, and the product is purified with a chromatography technique on silica gel. The product is eluted with methylene chloride. $R_f$=0.4. The yield of N-(5-chloropyridine-2-yl)-2-[4-methylamino-2-(3-aminopropoxy)-6-fluorophenylcarbonylamino]-5-chlorobenzamide is 160 mg.

Reaction 3

150 mg of N-(5-chloropyridine-2-yl)-2-[4-methylamino-2-(3-amino-propoxy)-6-fluorophenylcarbonylamino]-5-chlorobenzamide is dissolved with heating in 5 ml of acetonitrile. The obtained solution is cooled in ice, and a dry gaseous HCl is passed therethrough. In 30 min, the solution is placed in a refrigerator and allowed to stand at 5° C. for 48 hours. Then the reaction mixture is added with NaHCO$_3$ and stirred thoroughly. New portions of NaHCO$_3$ are added till the gas emission ceases. The solution obtained after neutralization of excess HCl is diluted with 10 ml of water and extracted three times with chloroform. The chloroform-treated extracts are joined together and evaporated. The residue is dissolved in water and titrated with 1% aqueous NaOH till pH=9. The solution is allowed to stand at 25° C. for 3 hours, neutralized, evaporated, and the residue is applied onto a 20×250 column filled with a reversed phase of C2 (RP2). The column is washed with 100 ml of water; then the elution is carried out with an ethyl alcohol gradient of from 0 to 50% against 1% aqueous acetic acid. The product yield is per about 30% of ethyl alcohol. The product purity is controlled with a TLC technique in a 3:5:2 acetonitrile/dioxane/aqueous ammonia system. $R_f$=0.5. The yield of N-(5-chloropyridine-2-yl)-2-[2-(3-aminopropoxy)-6-fluoro-4(ethaneamidoylmethylamino)phenylcarbonylamino]-5-chlorobenzamide is 60 mg. The mass spectrum (MALDI-VP): M+H 547, M+Na 569

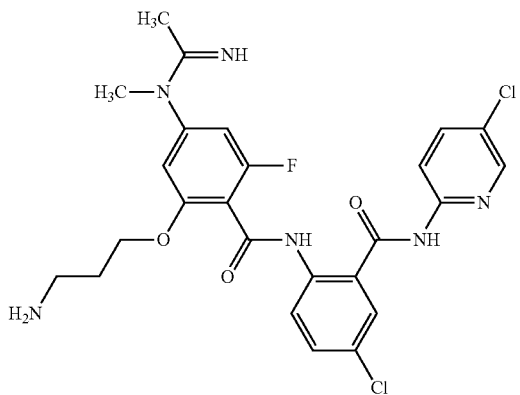 [SMILES: CC(=N)N(C)c1cc(F)c(C(=O)Nc2ccc(Cl)cc2C(=O)Nc2ccc(Cl)cn2)c(OCCCN)c1]

Example 11

Reaction 1

0.5 mg of 4-methylamino-2-fluorobenzoic acid is mixed with 1 ml of trifluoroacetic anhydride. In 1 hour the reaction mixture is evaporated, the residue is applied onto a 20×150 column filled with 40 to 60 µm of silica gel. The product is eluted in a 9:1 chloroform/ethanol system. The yield is 2-fluoro-4-[trifluoroacetyl(methyl)amino]benzoic acid is 470 mg.

Reaction 2

450 mg Of 2-amino-N-(5-chloropyridine-2-yl)-5-methylbenzamide, 480 mg of 2-fluoro-4-[trifluoroacetyl(methyl)amino]benzoic acid, and 500 mg of EDCI are mixed in 3 ml of THF and stirred for 48 hours. Then the reaction mixture is evaporated, the residue is applied onto a column containing silica gel, and the product is eluted with methylene chloride. $R_f$=0.5 (methylene chloride). The yield of N-(5-chloropyridine-2-yl)-2-[2-fluoro-4-trifluoroacetylmethyl)aminophenylcarbonylamino]5-methylbenzamide is 470 mg.

Reaction 3

450 mg of N-(5-chloropyridine-2-yl)-2-[2-fluoro-4-trifluoroacetylmethyl)aminophenylcarbonylamino]5-methylbenzamide are dissolved in a mixture of 300 µl of 3 M aqueous NaOH and 3 ml of ethanol and stirred for 1 hour; then the solution is neutralized, the residue is evaporated, and the product is purified with a chromatography technique on silica gel. The product is eluted with methylene chloride. $R_f$=0.2. The yield of N-(5-chloropyridine-2-yl)-2-[2-fluoro-4-methylaminophenylcarbonylamino]-5-methylbenzamide is 380 mg.

Reaction 4

350 mg of N-(5-chloropyridine-2-yl)-2-[2-fluoro-4-methylaminophenylcarbonylamino]-5-methylbenzamide are dissolved with heating in 5 ml of acetonitrile. The obtained solution is cooled with ice and dry gaseous HCl is passed therethrough. In 30 min, the solution is placed in a refrigerator and allowed to stand at 5° C. for 48 hours. Then the reaction mixture is added with NaHCO$_3$ and stirred thoroughly. New portions of NaHCO$_3$ are added till the emission of gasses ceases. The solution obtained after neutralization of excess HCl is diluted with 10 ml of water and extracted three times with chloroform. The chloroform-treated extracted are joined together and evaporated. The residue is dissolved in water and titrated with 1% aqueous NaOH till pH=9. The solution is allowed to stand at 25° C. for 3 hours, neutralized, evaporated, and the residue is applied onto a 20×250 column filled with a reversed phase of C2 (RP2). The column is washed with 100 ml of water; then the elution is carried out with an ethyl alcohol gradient of from 0 to 50% against the background of 1% aqueous acetic acid. The product yield is about per 30% of ethyl alcohol. The product purity is controlled with a TLC technique in a 9:1 dioxane/aqueous ammonia system. $R_f$=0.2. The yield of N-(5-chloropyridine-2-yl)-2-[2-fluoro-4-ethaneimidoylmethyl)amino)phenylcarbonylamino]5-methylbenzamide is 160 mg. The mass spectrum (MALDI-VP): M+H 454, M+Na 476.

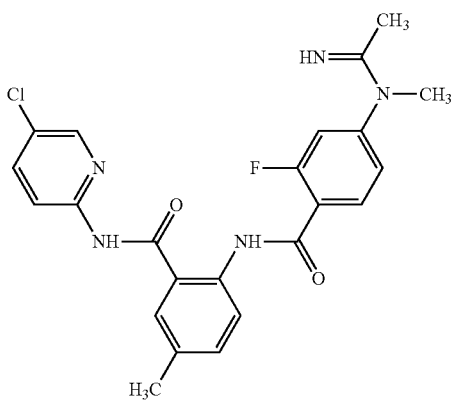

Example 12

Reaction 1

350 mg of 2-amino-N-(5-chloropyridine-2-yl)-5-chlorobenzamide, 370 mg of 2-fluoro-4-[trifluoro-acetyl(methylamino)]benzoic acid, and 390 mg of EDCI are mixed in 2 ml of THF and stirred for 48 hours. Then the reaction mixture is evaporated, the residue is applied onto a column with silica gel, and the product is eluted with methylene chloride. $R_f$=0.5 (methylene chloride). The yield of N-(5-chloropyridine-2-yl)-2-[2-fluoro-4-trifluoroacetyl(methyl)aminophenylcarbonylamino]-5-chlorobenzamide is 370 mg.

Reaction 2

350 mg of N-(5-chloropyridine-2-yl)-2-[2-fluoro-4-trifluoroacetylmethyl)aminophenylcarbonylamino]-5-chlorobenzamide are dissolved in a mixture of 300 μl of aqueous NaOH and 3 ml of ethanol and stirred for 1 hour; then the solution is neutralized, the residue is evaporated, and the product is purified with a chromatography technique on silica gel. The product is eluted with methylene chloride. $R_f$=0.4. The yield of N-(5-chloropyridine-2-yl)-2-[2-fluoro-4-methylaminophenylcarbonylamino]-5-chlorobenzamide is 320 mg.

Reaction 3

300 mg of N-(5-chloropyridine-2-yl)-2-[2-fluoro-4-methylaminophenylcarbonylamino]-5-chlorobenzamide are dissolved with heating in 5 ml of acetonitrile. The obtained solution is cooled in ice and a dry gaseous HCl is passed therethrough. In 30 min, the solution is placed in a refrigerator and allowed to stand at 5° C. for 48 hours. Then the reaction mixture is added with $NaHCO_3$ and stirred thoroughly. New portions of $NaHCO_3$ are added till the emission of gasses ceases. The solution obtained after neutralization of excess HCl is diluted with 10 ml of water and extracted three times with chloroform. The chloroform-treated extracts are joined together and evaporated. The residue is dissolved in water and titrated with 1% NaOh till pH=9. The solution is allowed to stand at 25° C. for 3 hours, neutralized, evaporated, and the residue is applied onto a 2-×250 column filled with a reversed phase of C2(RP2). The column is washed with 100 ml of water; then the elution is carried out with a gradient of ethyl alcohol of from 0 to 50% against the background of aqueous acetic acid. The product yield is about per 30% of ethyl alcohol. The product purity is controlled with a TLC technique in a 9:1 dioxane/aqueous ammonia system. $R_f$=0.2. The yield of N-(5-chloropyridine-2-yl)-2-[2-fluoro-4-(ethaneimidoylmethyl)amino)phenylcarbonylamino]-5-chlorobenzamide is 140 mg. The mass spectrum (MALDI-VP): M+H 474, M+Na 496.

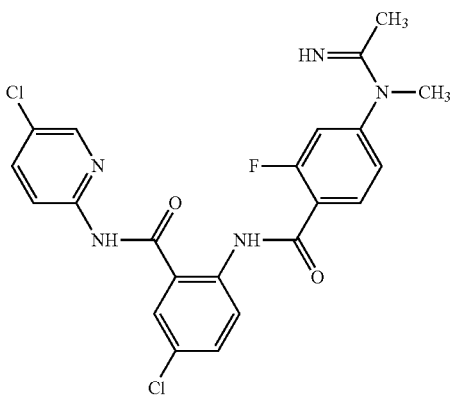 [SMILES: CC(=N)N(C)c1ccc(C(=O)Nc2ccc(Cl)cc2C(=O)Nc2ccc(Cl)cn2)c(F)c1]

Example 13

Reaction 1

90 mg of 2-[3-(acetylamino)propoxy]-4-(methylamino)benzoic acid are mixed with 1 ml of trifluoroacetic anhydride. In 1 hour the reaction mixture is evaporated, the residue is applied onto a 20×150 column filled with 40 to 60 μm of silica gel. The product is eluted in a 9:1 chloroform/ethanol system. The yield of 2-[3-(acetylamino)propoxy]-4-[trifluoroacetylmethyl)amino)]benzoic acid is 100 mg.

Reaction 2

90 mg of 2-amino-N-(5-chloropyridine-2-yl)-5-methylbenzamide, 95 mg of 2-[3-(acetylamino)propoxy]-4-[trifluoroacetyl(methyl)amino]benzoic acid, and 80 mg of EDCI are mixed in 1 ml of THF and stirred for 48 hours. Then the reaction mixture is evaporated, the residue is applied onto a column containing silica gel, and the product is eluted with methylene chloride. $R_f$=0.5 (methylene chloride). The yield of N-(5-chloropyridine-2-yl)-2-[4-(trifluoroacetyl(methyl)amino)-2-(3-(acetylamino)propoxy)phenylcarbonylamino]-5-methylbenzamide is 80 mg.

Reaction 3

70 mg of N-(5-chloropyridine-2-yl)-2-[4-(trifluoroacetylmethyl)amino)-2-(3-(acetylamino)propoxy)phenylcarbonylamino]-5-methylbenzamide is dissolved in a mixture of 100 μl of 3M aqueous NaOH and 1 ml of ethanol and stirred for 1 hour; then the solution is neutralized, the residue is evaporated, and the product is purified with a chromatography technique on silica gel. The product is eluted with methylene chloride. $R_f$=0.4. The yield of N-(5-chloropyridine-2-yl)-2-[4-methylamino-2-(3-(acetylamino)propoxy)phenylcarbonylamino]-5-methylbenzamide is 55 mg.

Reaction 4

50 mg of N-(5-chloropyridine-2-yl)-2-[4-methylamino-2-(3-(acetylamino)propoxy)phenylcarbonylamino]-5-methylbenzamide is dissolved with heating in 2 ml of acetonitrile. The obtained solution is cooled in ice and a dry aqueous HCl is passed therethrough. In 30 min the solution is placed in a refrigerator and allowed to stand at 5° C. for 48 hours. Then the reaction mixture is added with $NaHCO_3$ and stirred thoroughly. New portion of $NaHCO_3$ are added till the gas emission ceases. The solution obtained after neutralization of excess HCl is diluted with 5 ml of water and extracted with chloroform three times. The chloroform-treated extracts are joined together and evaporated. The residue is dissolved in water and titrated with 1% aqueous NaOH till pH=9. The solution is allowed to stand at 25° C. for 3 hours, neutralized, evaporated, and the residue is applied onto a 20×250 column filled with a reversed phase of C2 (RP2). The column is washed with 100 ml of water and the elution is carried out with a gradient of ethyl alcohol of from 0 to 50% against the background of 1% aqueous acetic acid. The product yield is about per 30% of ethyl alcohol. The product purity is controlled with a TLC techniques in a 9:1 dioxane/aqueous ammonia system. $R_f$=0.3. The yield of N-(5-chloropyridine-2-yl)-2-[4-(ethaneimidoylmethylamino)-2-(3-(acetylamino)propoxy)phenylcarbonylamino]-5-methylbenzamide is 20 mg. The mass spectrum (MALDI-VP): M+H 551, M+Na 573.

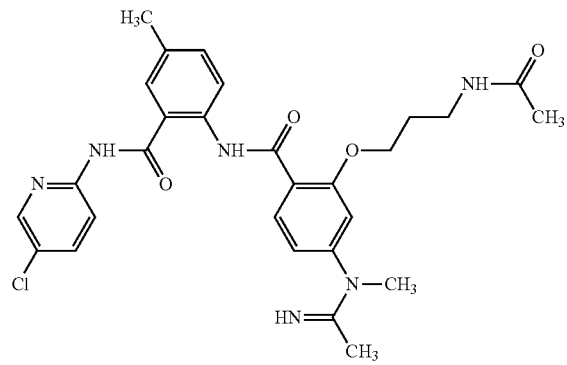 [SMILES: CC(=N)N(C)c1ccc(C(=O)Nc2ccc(C)cc2C(=O)Nc2ccc(Cl)cn2)c(OCCCNC(C)=O)c1]

Example 14

Reaction 1

100 mg of N-(5-chloropyridine-2-yl)-2-[(4-methylaminophenylcarbonyl)amino]-5-methylbenzamide and 150 mg of sodium cyanate are mixed in 1 ml of THF and added with 300 μm of acetic acid. The reaction mixture are stirred for 24 hours. Then the reaction mixture is evaporated, the residue is applied onto a column containing silica gel, and the product is eluted with chloroform. $R_f$=0.25 (chloroform). The yield of N-(5-chloropyridine-2-yl)-2-[(4-carbamoyl(methyl)aminophenylcarbonyl)amino]-5-methylbanzamide is 70 mg.

Reaction 2

60 mg of N-(5-chloropyridine-2-yl)-2-[(4-carbamoyl(methyl)aminophenylcarbonyl)amino]-5-methylbanzamide are dissolved in 2 ml of THF and the solution is added with 200 μl of dimethylsulfate. The reaction mixture is stirred for 24 hours, evaporated, and the residue is subjected to chromatographic separation on silica gel. N-(5-chloropyridine-2-yl)-2-[(4-(imino(methoxy)methyl)(methyl)aminophenylcarbonyl)amino]5-methylbenzamide is eluted with chloroform. The yield is 40 mg. $R_f$=0.4 (chloroform). The mass spectrum (MALDI-VP): M+H 452, M+Na 474.

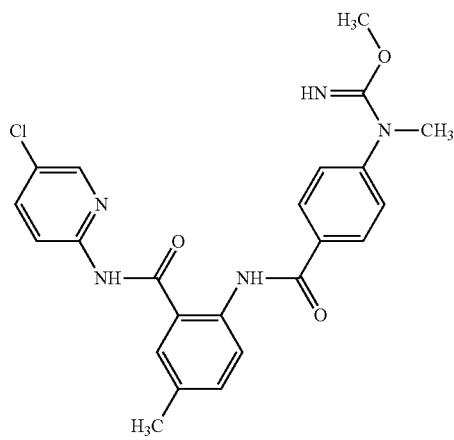 [SMILES: COC(=N)N(C)c1ccc(C(=O)Nc2ccc(C)cc2C(=O)Nc2ccc(Cl)cn2)cc1]

Example 15

Reaction 1

250 mg of N-(5-chloropyridine-2-yl)-2-[(4-methylaminophenyl-carbonyl)amino]-5-methylbenzamide, 290 mg of 4-benzyl-3,5-dimethyl-1H pyrazole-1-carboxamidine hydrochloride, and 130 μl triethylamine are mixed in acetonitrile and allowed to stand at 60° C. for 24 hours. Then the reaction mixture is evaporated and separated with a chromatography technique on the reversed phase of C2. The product is eluted with an ethanol gradient against the background of 1% aqueous acetic acid. The yield of 2-[4-carbamimidoylmethylamino]phenylcarbonylamino]-N-(5-chloropyridine-2-yl)-5-methylbenzamide is 150 mg.

Reaction 2

120 mg of 2-[4-carbamimidoylmethylamino]phenylcarbonylamino]-N-(5-chloropyridine-2-yl)5-methylbenzamide are dissolved in 2 ml of THF and added with 100 μl of methyl iodide and 150 mg of $K_2CO_3$. The reaction mixture is heated to 50° C. and allowed to stand for 10 hours. Then the reaction mixture is evaporated, the residue is separated with a chromatography technique on the reversed phase of C2. The yield of 2-[4-(methyl(N-methylcarbamimidoyl)-amino)]phenylcarbonylamino]-N-(5-chloropyridine-2-yl)-5-methylbenzamide is 70 mg. $R_f$=0.3 (8:2 dioxane/aqueous ammonia). The mass spectrum (MALDI-VP): M+H 451, M+Na 473.

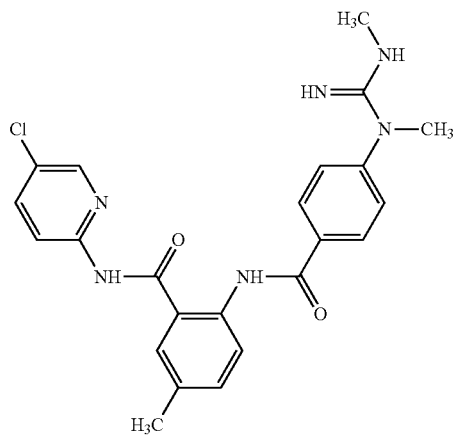 [SMILES: CNC(=N)N(C)c1ccc(C(=O)Nc2ccc(C)cc2C(=O)Nc2ccc(Cl)cn2)cc1]

Example 16

Reaction 1

250 mg of N-(5-chloropyridine-2-yl)-2-[(4-methylamino-phenyl-carbonyl)amino]-5-chlorobenzamide, 290 mg of 4-benzyl-3,5-dimethyl-1H pyrazole-1-carboxamidine hydrochloride, and 130 µl of triethylamine are mixed in acetonitrile and allowed to stand at 60° C. for 24 hours. Then the reaction mixture is evaporated and separated with a chromatography technique on the reversed phase of C2. The product is eluted with an ethanol gradient against the background of 1% aqueous acetic acid. The yield of 2-[4-carbamimidoylmethylamino]phenylcarbonylamino]-N-(5-chloropyridine-2-yl)-5-chlorobenzamide is 150 mg.

Reaction 2

120 mg of 2-[4-carbamimidoylmethylamino]phenylcarbonylamino]-N-(5-chloropyridine-2-yl)5-chlorobenzamide are dissolved in 2 ml of THF and added with 100 nl of methyl iodide and 150 mg of $K_2CO_3$. The reaction mixture is heated to 50° C. and allowed to stand for 10 hours. Then the reaction mixture is evaporated, the residue is separated with a chromatography technique on the reversed phase of C2. The yield of 2-[4-(methyl(N-methylcarbamimidoyl)-amino)]phenylcarbonylamino]-N-(5-chloro-pyridine-2-yl)-5-chlorobenzamide is 70 mg. $R_f$=0.3 (8:2 dioxane/aqueous ammonia). The mass spectrum (MALDI-VP): M+H 471, M+Na 493.

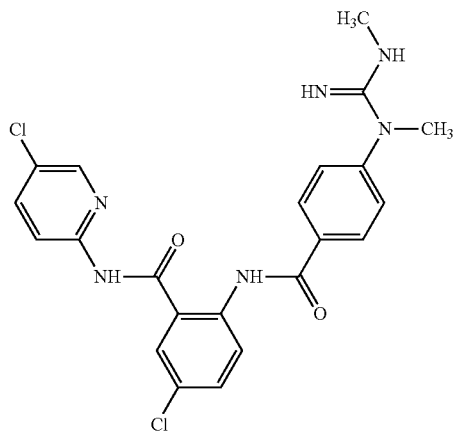 [SMILES: CNC(=N)N(C)c1ccc(C(=O)Nc2ccc(Cl)cc2C(=O)Nc2ccc(Cl)cn2)cc1]

Example 17

Reaction 1

A solution of 750 mg of 4-methylaminobenzoic acid in 10 ml of THF is added with 700 µl of methylisocyanate. The reaction mixture is stirred at room temperature for 72 hours, evaporated, and reevaporated with water. The product is recrystallized from isopropanol. The yield of 4-[methyl (methylcarbamoyl)amino]benzoic acid is 700 mg.

Reaction 2

300 mg of 4-[methylmethylcarbamoyl)amino]benzoic acid, 250 mg of 2-amino-N-(5-chloropyridine-2-yl)-5-chlorobenzamide, and 300 mg of EDCI in 2 ml of THF are stirred for 72 hours. Then the reaction mixture is evaporated, the residue is separated with a chromatography technique on silica gel. The column is washed with chloroform and then with 9:1 chloroform/ethanol. $R_f$=0.5 (chloroform). The yield of N-(5-chloropyridine-2-yl)-2-[(4-methyl(methylcarbamoyl)aminophenylcarbonyl)amino]-5-chlorobenzamide is 280 mg. $R_f$=0.3 (8:2 dioxane/aqueous ammonia). The mass spectrum (MALDI-VP): M+H 472, M+Na 494.

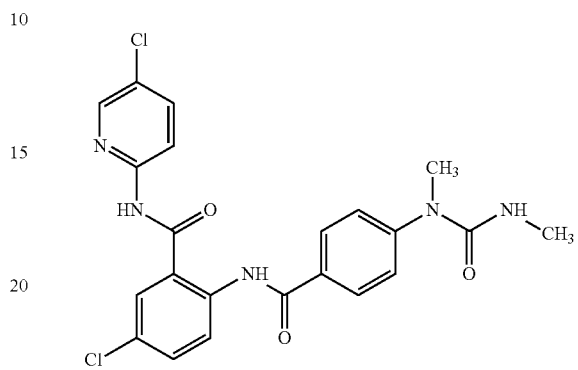

Example 18

240 mg of 4-[methylmethylcarbamoyl)amino]benzoic acid, 220 mg of 2-amino-N-(5-chloropyridine-2-yl)-5-methylbenzamide, and 250 mg of EDCI in 2 ml of THF is stirred for 48 hours. Then the reaction mixture is evaporated, the residue is separated with a chromatography technique. The yield of N-(5-chloropyridine-2-yl)-2-[(4-methyl(methylcarbamoyl)aminophenyl-carbonyl)amino-5-methylbenzamide is 250 mg. $R_f$=0.55 (chloroform). The mass spectrum (MALDI-VP): M+H 452, M+Na 474.

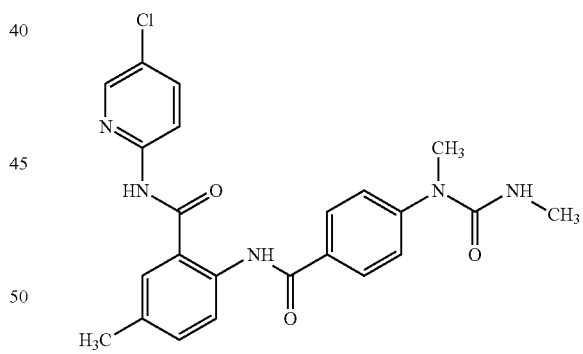

Reaction 1

A mixture of 0.5 g of 4-[tertbutoxycarbonyl(methyl) amino]salicylic acid, 0.6 g of N-(3-chloropropyl)-trifluoroacetylamide, and 0.5 g of $K_2CO_3$ are heated to 110° C. In 1 hour the reaction mixture is cooled, diluted with water, and extracted with chloroform; the extract is evaporated and applied onto a 30×150 column filled with 40 to 60 µm of silica gel; the product is eluted with a 9:1 chloroform/ethanol mixture. $R_f$=0.5 (9:1 chloroform/ethanol). The yield of 2-[3-(trifluoroacetylamino)-propoxy]-4-[(tert-butoxycarbonyl)(methyl)amino]benzoic acid is 350 mg.

35

Reaction 2

320 mg of 2-[3-(trifluoroacetylamino)-propoxy]-4-[(tert-butoxycarbonyl)(methyl)amino]benzoic acid are dissolved in 2 ml of ethanol and added with 200 µl of 10% aqueous HCl, the solution is stirred for 3 hour, then the reaction mixture is neutralized, evaporated, and the residue is separated with a chromatography technique on silica gel in a 9:1 chloroform/ethanol mixture. The yield of 2-[3-(trifluoroacetylamino)-propoxy]-4-(methyl)aminobenzoic acid is 250 mg.

Reaction 3

220 mg of 2-[3-(trifluoroacetylamino)-propoxy]-4-(methyl)aminobenzoic acid are dissolved in 5 ml of THF and added with 300 µl of methylisocyanate. In 78 hours the reaction mixture is evaporated, the residue is separated with a chromatography technique on silica gel in a 9:1 chloroform/ethanol mixture. The yield of 4-[methyl(methylcarbamoyl)amino]-2-[3-(trifluoroacetyl-amino)propoxybenzoic acid is 230 mg.

Reaction 4

200 mg of 4-[methylmethylcarbamoyl)amino]-2-[3-(trifluoroacetyl-amino)propoxybenzoic acid (377), 140 mg of 2-amino-N-(5-chloropyridine-2-yl)-5-methylbenzamide (262), and 150 mg of EDCI in 2 ml of THF are stirred for 48 hours. Then the reaction mixture is evaporated, the residue is separated with a chromatography technique. The yield of N-(5-chloropyridine-2-yl)-2-{[4-methylmethylcarbamoyl)-amino]-2-[3-(trifluoroacetyl-amino)propoxy]phenylcarbonyl}amino]-5-methylbenzamide is 210 mg. $R_f$=0.5 (chloroform).

Reaction 5

190 mg of N-(5-chloropyridine-2-yl)-2-{[4-methyl(methylcarbamoyl)-amino]-2-[3-(trifluoroacetyl-amino)propoxy]phenylcarbonyl}amino]-5-methylbenzamide are dissolved in 2 ml of ethanol, added with 200 ml of 10% aqueous NaOH. In 2 hours the reaction mixture is evaporated and separated with a chromatography technique on silica gel. $R_f$=0.45 (chloroform). The yield of N-(5-chloropyridine-2-yl)-2-{[4-methyl(methylcarbamoyl)-amino]-2-[3-amino-propoxy]phenylcarbonyl}amino]-5-methylbenzamide is 160 mg. The mass spectrum (MALDI-VP): M+H 525, M+Na 547.

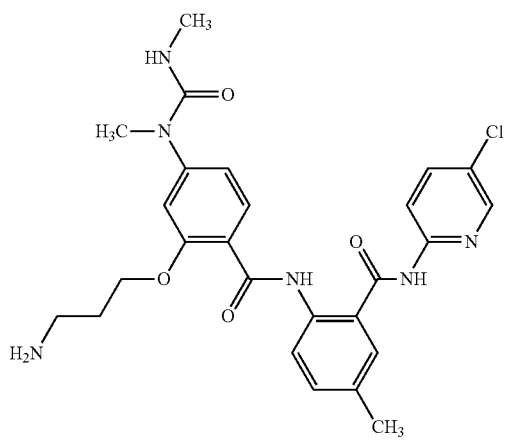 [SMILES: CNC(=O)N(C)c1ccc(C(=O)Nc2ccc(C)cc2C(=O)Nc2ccc(Cl)cn2)c(OCCCN)c1]

36

Example 20

Reaction 1

200 g of -[4-methyl(methylcarbamoyl)-amino-2-[3-(trifluoroacetyl-amino)]propoxybenzoic acid, 140 mg of 2-amino-N-(5-chloropyridine-2-yl)-5-chlorobenzamide, and 150 mg of EDCi in 2 ml of THF are stirred for 48 hours. Then the reaction mixture is evaporated, the residue is separated with a chromatography technique. The yield of N-(5-chloropyridine-2-yl)-2-{[4-methylmethylcarbamoyl)-amino]-2-[3-trifluoroacetyl-amino)propoxy]phenylcarbonyl}amino]-5-chlorobenzamide is 210 mg. $R_f$=0.5 (chloroform).

Reaction 2

190 mg of N-(5-chloropyridine-2-yl)-2-{[4-methyl(methylcarbamoyl)-amino]-2-[3-trifluoroacetyl-amino)propoxy]phenylcarbonyl}amino]-5-chlorobenzamide are dissolved in 2 ml of ethanol and added with 200 ml of 10% aqueous NaOH. In 2 hours the reaction mixture is evaporated and separated with a chromatography technique on silica gel. $R_f$=0.45 (chloroform). The yield of N-(5-chloropyridine-2-yl)-2-{[4-methyl(methylcarbamoyl)-amino]-2-[3-amino-propoxy]phenylcarbonyl}amino]-5-chlorobenzamide is 160 mg. The mass spectrum (MALDI-VP): M+H 545, M+Na 567.

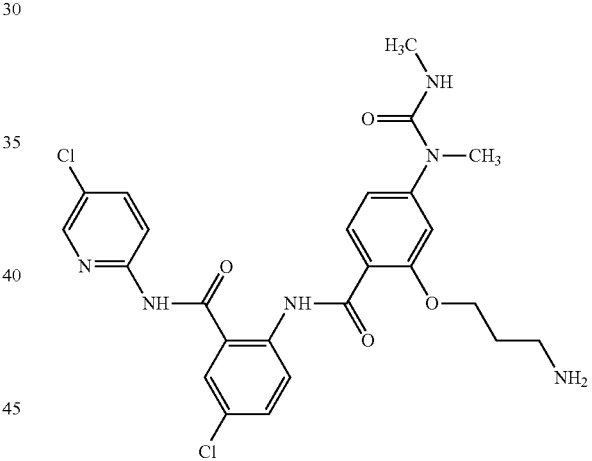

The Activity of Substances Towards the Factor Xa In Vitro

For some compounds depicted in the above examples, there has been measured a constant of activity of these substances towards the factor Xa in vitro—$K_i$. The measurements were carried out kinetically, in terms of the initial rate of decomposition of the substrate S-2222 by the protein. The measurements were carried out at room temperature in 2 ml rectangular quartz cuvettes. In the reaction there was used a solution: 50 mM Tris-HCl, 150 mM NaCl, 2.5 mM $CaCl_2$, and 0.1% PEG 6000, pH 7.5, factor Xa 0.04-1 nm, S-2222 164 µM. The standard least-squares method was used for determining $K_m$ for certain concentrations of the protein and substrate. Before the reaction, the protein and the active agent in the solution were under thermostatic control for 10 min; then the substrate was added and the reaction was initiated. The reaction rate was measured with a Specord M80 instrument from a change in the light absorption at a wavelength of 405 nm. The $IC_{50}$ values were determined from the experimentally obtained dependence of the initial rates on the concentration of the inhibitor (active agent). The $K_i$ values were calculated from the concentrations of the protein, substrate, and inhibitors; the $IC_{50}$ values, by the method described in (1) Jordan, S. P.; Waxman, L.; Smith, D. E.; Vlasik, G. P. Biochemistry 1990, 29, 11095 and (2) Morrison, J. F. Biochim Biophys. Acta 1969, 185, 269. The results are shown in Table 1.

TABLE 1

The activity constant $K_i$ of compounds towards the protein Xa in vitro.

| Substance | Ki, nM |
|---|---|
| Example 1 | 2.0 |
| Example 2 | 0.5 |
| Example 3 | 0.3 |
| Example 4 | 1.0 |
| Example 5 | 0.5 |
| Example 6 | 0.5 |
| Example 7 | 0.5 |
| Example 8 | 0.5 |
| Example 9 | 0.4 |
| Example 10 | 0.4 |
| Example 11 | 0.8 |
| Example 12 | 1.0 |
| Example 13 | 0.5 |
| Example 14 | 2.0 |
| Example 15 | 0.5 |
| Example 16 | 0.5 |
| Example 17 | 0.15 |
| Example 18 | 0.15 |
| Example 19 | 0.2 |
| Example 20 | 0.2 |

The Activity of Substances in Human Blood Plasma Towards the Prothrombin Time In Vitro For some compounds depicted in the above examples, there has been measured the concentration of these compounds in human blood plasma, at which the prothrombin time of plasma is twice as much—2PT. The measurements were carried out with the aid of a Diahem P kit (NPO Renam, www.renam.ru) by a method described in the instruction for users of the kit. The active compound was dissolved in a blood plasma provided in the kit and was incubated for 3 min. The measurements were carried out with a Sysmex CA 50 instrument. For each concentration, there were taken 3 measurements and the result was averaged. The results are shown in Table 2.

TABLE 2

The activity constant $K_i$ of compounds towards the protein Xa in blood plasma.

| Substance | 2 × PT, µM |
|---|---|
| Example 1 | 0.5 |
| Example 2 | 0.08 |
| Example 3 | 0.12 |
| Example 4 | 0.1 |
| Example 5 | 0.2 |
| Example 6 | 0.2 |
| Example 7 | 0.2 |
| Example 8 | 0.2 |
| Example 9 | 0.15 |
| Example 10 | 0.15 |
| Example 11 | 0.09 |
| Example 12 | 0.09 |
| Example 13 | 1.5 |
| Example 14 | 5.0 |
| Example 15 | 1.5 |
| Example 16 | 1.5 |
| Example 17 | 2.0 |
| Example 18 | 3.0 |
| Example 19 | 1.0 |
| Example 20 | 1.0 |

What is claimed is:

1. A pharmaceutical composition comprising a compound of formula I,

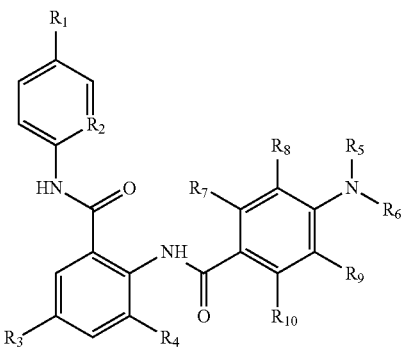

wherein:
$R_1$ is selected from the group consisting of H, —Cl, —F, —Br, —OH, -Me, and —OMe;
$R_2$ is selected from the group consisting of CH and N;
$R_3$ and $R_4$ are each independently selected from the group consisting of H, —Cl, —F, —Br, —OH, -Me, and —OMe;
$R_5$ is H or a C1-C6 alkyl which is optionally substituted with a hydroxyl, carboxylic acid or carboxylic acid ester group;
$R_6$ is selected from the group consisting of:

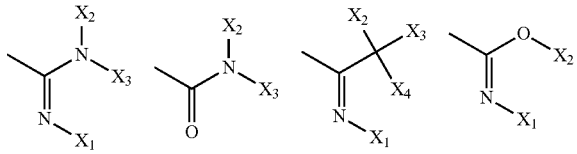

wherein:
$X_1$, $X_2$, $X_3$ and $X_4$ are each independently H or a C1-C6 alkyl which is optionally substituted with a hydroxyl, carboxylic acid or carboxylic acid ester group;
$R_8$, $R_9$ and $R_{10}$ are each independently selected from the group consisting of H, —Cl, —F, —Br, —OH, -Me, and —OMe; and
$R_7$ is selected from the group consisting of H, —Cl, —F, —Br, —OH, -Me, —OMe, and:

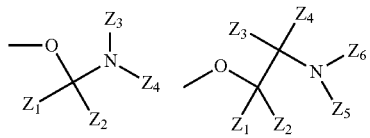

-continued

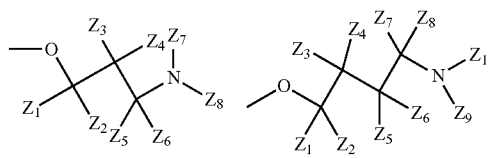

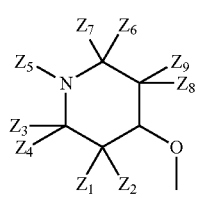

wherein $Z_1$, $Z_2$, $Z_3$, $Z_4$, $Z_5$, $Z_6$, $Z_7$, $Z_8$, $Z_9$ and $Z_{10}$ are each independently H or a C1-C6 alkyl which is optionally substituted with a hydroxyl, carboxylic acid or carboxylic acid ester group.

2. The pharmaceutical composition of claim 1 comprising a compound of the following structure:

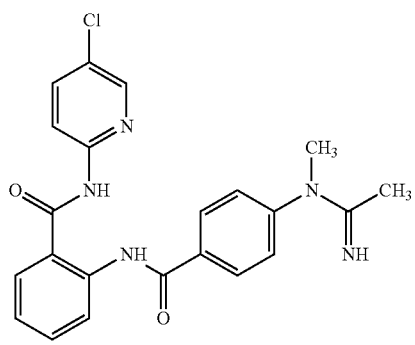 [SMILES: CC(=N)N(C)c1ccc(C(=O)Nc2ccccc2C(=O)Nc2ccc(Cl)cn2)cc1]

3. The pharmaceutical composition of claim 1 comprising a compound of the following structure:

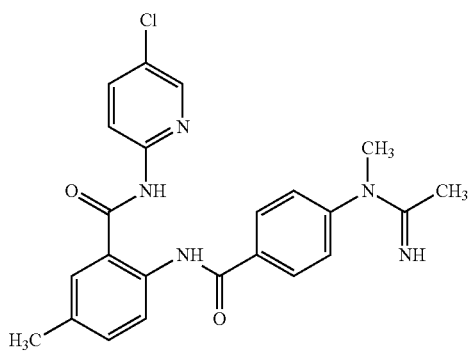

4. The pharmaceutical composition of claim 1 comprising a compound of the following structure:

5. The pharmaceutical composition of claim 1 comprising a compound of the following structure:

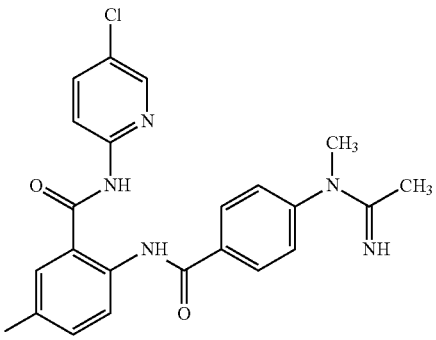

6. The pharmaceutical composition of claim 1 comprising a compound of the following structure:

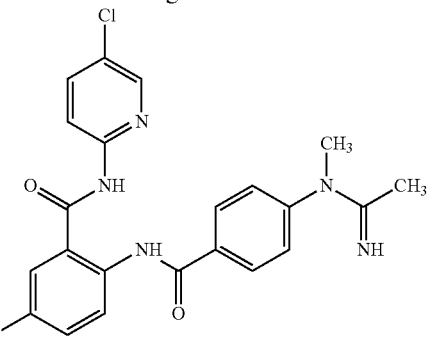

7. The pharmaceutical composition of claim 1 comprising a compound of the following structure:

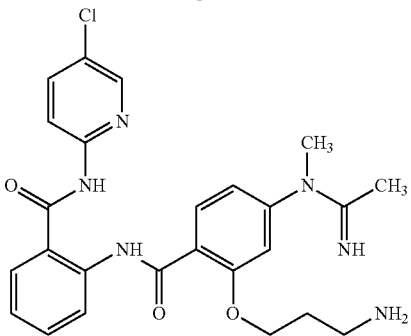 [SMILES: CC(=N)N(C)c1ccc(C(=O)Nc2ccccc2C(=O)Nc2ccc(Cl)cn2)c(OCCCN)c1]

8. The pharmaceutical composition of claim 1 comprising a compound of the following structure:

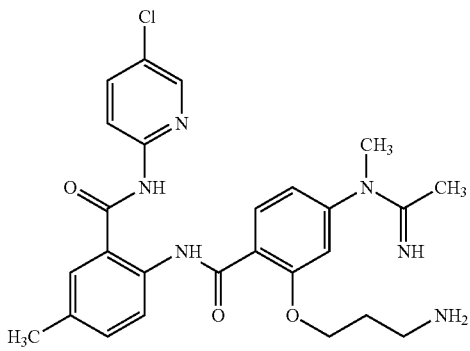 [SMILES: CC(=N)N(C)c1ccc(C(=O)Nc2ccc(C)cc2C(=O)Nc2ccc(Cl)cn2)c(OCCCN)c1]

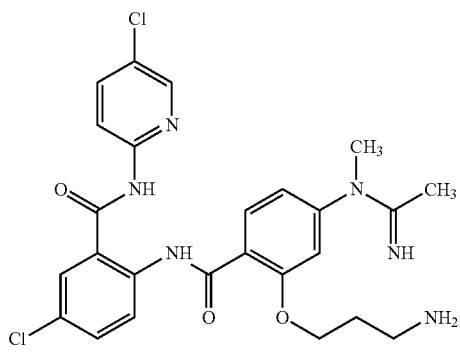 [SMILES: CC(=N)N(C)c1ccc(C(=O)Nc2ccc(Cl)cc2C(=O)Nc2ccc(Cl)cn2)c(OCCCN)c1]

9. The pharmaceutical composition of claim 1 comprising a compound of the following structure:

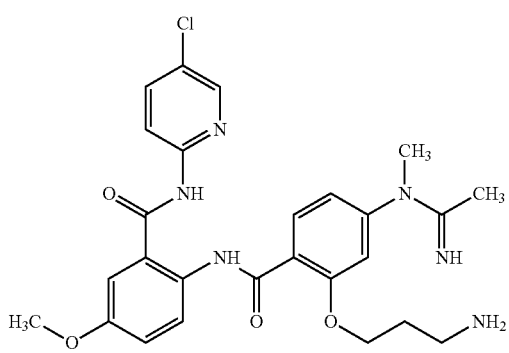 [SMILES: COc1ccc(NC(=O)c2ccc(N(C)C(C)=N)cc2OCCCN)c(C(=O)Nc2ccc(Cl)cn2)c1]

10. The pharmaceutical composition of claim 1 comprising a compound of the following structure:

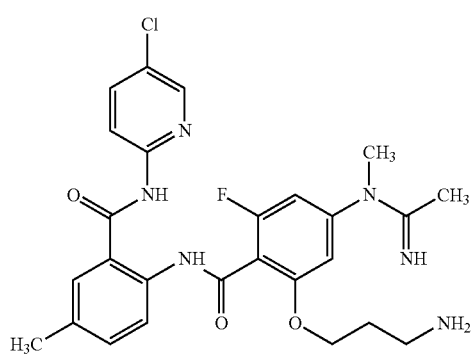 [SMILES: CC(=N)N(C)c1cc(F)c(C(=O)Nc2ccc(C)cc2C(=O)Nc2ccc(Cl)cn2)c(OCCCN)c1]

11. The pharmaceutical composition of claim 1 comprising a compound of the following structure:

12. The pharmaceutical composition of claim 1 comprising a compound of the following structure:

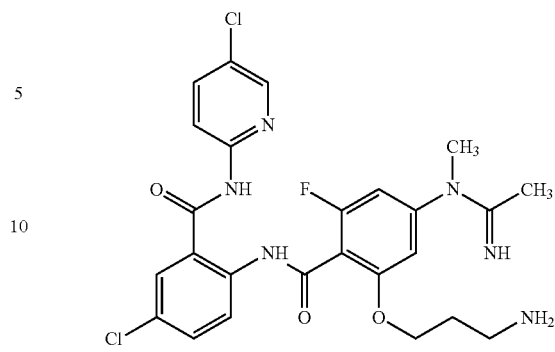

13. The pharmaceutical composition of claim 1 comprising a compound of the following structure:

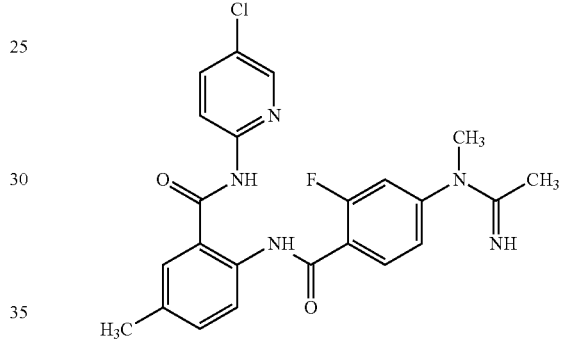

14. The pharmaceutical composition of claim 1 comprising a compound of the following structure:

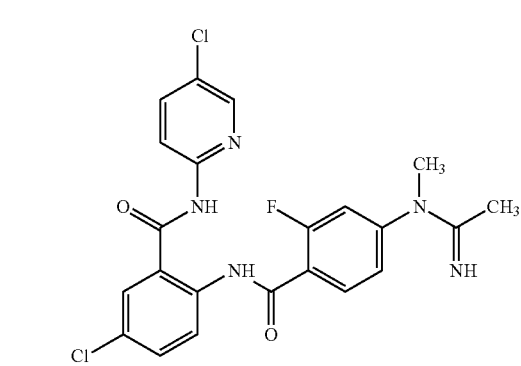 [SMILES: CC(=N)N(C)c1ccc(C(=O)Nc2ccc(Cl)cc2C(=O)Nc2ccc(Cl)cn2)c(F)c1]

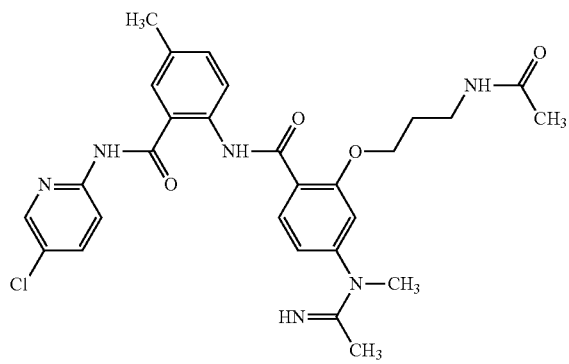 [SMILES: CC(=N)N(C)c1ccc(C(=O)Nc2ccc(C)cc2C(=O)Nc2ccc(Cl)cn2)c(OCCCNC(C)=O)c1]

15. The pharmaceutical composition of claim 1 comprising a compound of the following structure:

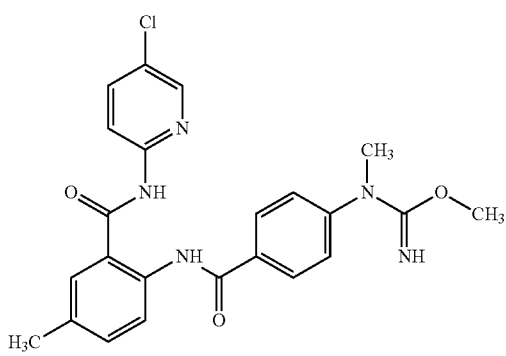

16. The pharmaceutical composition of claim 1 comprising a compound of the following structure:

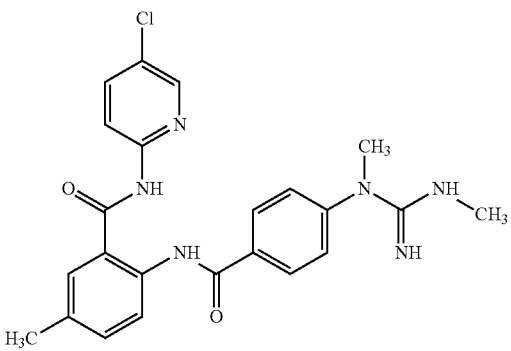

17. The pharmaceutical composition of claim 1 comprising a compound of the following structure:

18. The pharmaceutical composition of claim 1 comprising a compound of the following structure:

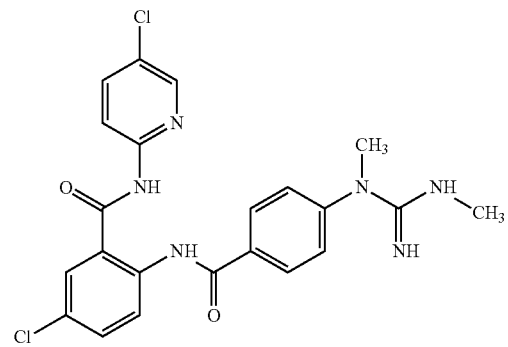 [SMILES: CNC(=N)N(C)c1ccc(C(=O)Nc2ccc(Cl)cc2C(=O)Nc2ccc(Cl)cn2)cc1]

19. The pharmaceutical composition of claim 1 comprising a compound of the following structure:

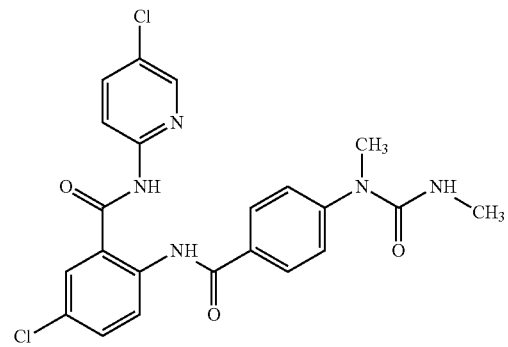 [SMILES: CNC(=O)N(C)c1ccc(C(=O)Nc2ccc(Cl)cc2C(=O)Nc2ccc(Cl)cn2)cc1]

20. The pharmaceutical composition of claim 1 comprising a compound of the following structure:

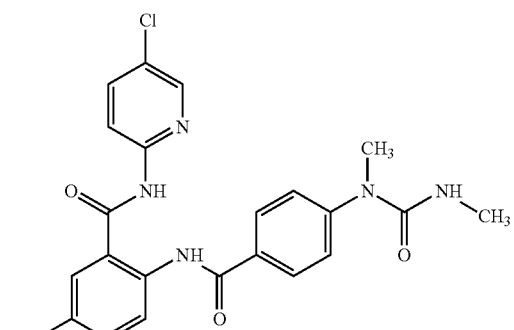

21. The pharmaceutical composition of claim 1 comprising a compound of the following structure:

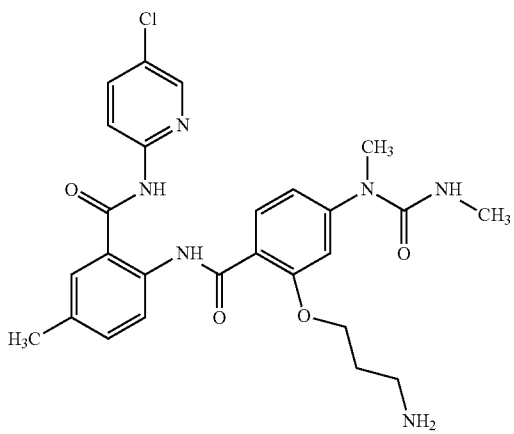

22. A pharmaceutical composition for preventing or treating a condition in a mammal characterized by undesired thrombosis comprising a pharmaceutically acceptable carrier and a therapeutically effective amount of the pharmaceutical composition of claim 1.

23. The pharmaceutical composition of claim 1 comprising a compound of the following structure:

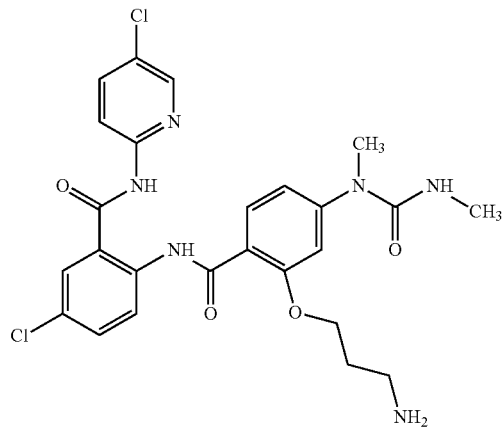 [SMILES: CNC(=O)N(C)c1ccc(C(=O)Nc2ccc(Cl)cc2C(=O)Nc2ccc(Cl)cn2)c(OCCCN)c1]

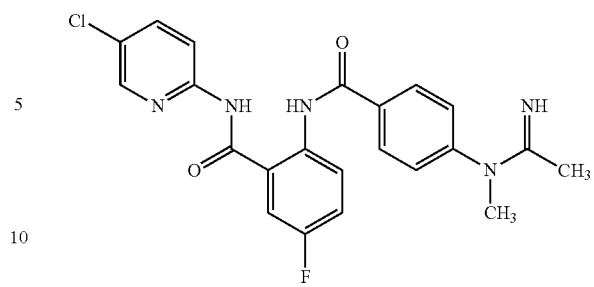

24. The pharmaceutical composition of claim 1 comprising a compound of the following structure:

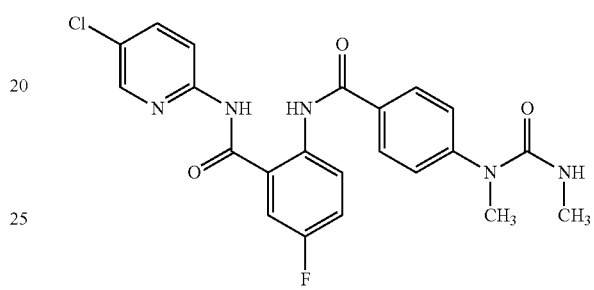

25. The pharmaceutical composition of claim 1 comprising a compound of the following structure:

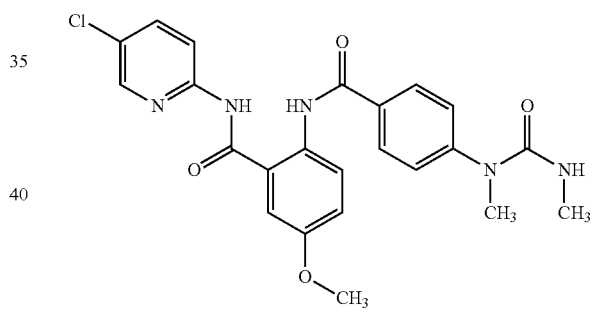

* * * * *